(12) United States Patent
Nishimura et al.

(10) Patent No.: US 9,428,505 B2
(45) Date of Patent: Aug. 30, 2016

(54) HYDANTOIN DERIVATIVE

(71) Applicant: Chugai Seiyaku Kabushiki Kaisha, Kita-ku, Tokyo (JP)

(72) Inventors: Yoshikazu Nishimura, Shizuoka (JP); Toru Esaki, Shizuoka (JP); Tatsuya Tamura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/426,408

(22) PCT Filed: Dec. 10, 2013

(86) PCT No.: PCT/JP2013/083022
§ 371 (c)(1),
(2) Date: Mar. 6, 2015

(87) PCT Pub. No.: WO2014/092061
PCT Pub. Date: Jun. 19, 2014

(65) Prior Publication Data
US 2015/0274727 A1 Oct. 1, 2015

(30) Foreign Application Priority Data

Dec. 10, 2012 (JP) ................................. 2012-269178

(51) Int. Cl.
*C07D 471/10* (2006.01)
*C07D 519/00* (2006.01)

(52) U.S. Cl.
CPC ........... *C07D 471/10* (2013.01); *C07D 519/00* (2013.01)

(58) Field of Classification Search
CPC . C07D 471/10; C07D 519/00; A61K 31/438
USPC ..................... 546/18, 20; 514/278
See application file for complete search history.

(56) References Cited

U.S. PATENT DOCUMENTS

| 7,666,892 B2 | 2/2010 | Eriksson et al. | |
|---|---|---|---|
| 7,981,904 B2 | 7/2011 | Chang et al. | |
| 8,476,286 B2 | 7/2013 | Beerli et al. | |
| 8,513,193 B2 | 8/2013 | Rosier et al. | |
| 2005/0101574 A1 | 5/2005 | Ishizuka et al. | |
| 2007/0099940 A1 | 5/2007 | Spearing | |
| 2007/0123548 A1 | 5/2007 | Cowan et al. | |
| 2012/0270838 A1* | 10/2012 | Esaki .................. | C07D 471/10 514/63 |

FOREIGN PATENT DOCUMENTS

| CN | 1516587 A | 7/2004 |
|---|---|---|
| EP | 1321141 A1 | 6/2003 |
| JP | 11-035470 A | 2/1999 |
| JP | 2004-523583 A | 8/2004 |
| JP | 2005-502605 A | 1/2005 |
| JP | 2007-522214 A | 8/2007 |
| JP | 2007-522215 A | 8/2007 |
| JP | 2008-515895 A | 5/2008 |
| WO | WO 00/35885 A1 | 6/2000 |
| WO | WO 02/17911 A1 | 3/2002 |
| WO | WO 02/074751 A1 | 9/2002 |
| WO | WO 02/102782 A2 | 12/2002 |
| WO | WO 2005/077918 A1 | 8/2005 |
| WO | WO 2005/077959 A1 | 8/2005 |
| WO | WO 2006/041830 A2 | 4/2006 |
| WO | WO 2007/135417 A1 | 11/2007 |
| WO | WO 2007/149873 A2 | 12/2007 |
| WO | WO 2008/148689 A1 | 12/2008 |
| WO | WO 2009/074575 A2 | 6/2009 |
| WO | 2010/126030 | * 11/2010 |
| WO | WO 2010/126030 A1 | 11/2010 |

OTHER PUBLICATIONS

Abou-Samra et al., "Expression cloning of a common receptor for parathyroid hormone and parathyroid hormone-related peptide from rat osteoblast-like cells: A single receptor stimulates intracellular accumulation of both cAMP and inositol trisphosphates and increases intracellular free calcium," Proc. Nat. Acad. Sci. USA, Apr. 1992, 89(7):2732-2736.
Bergwitz et al., "Full Activation of Chimeric Receptors by Hybrids between Parathyroid Hormone and Calcitonin," J. Biol. Chem., Oct. 25, 1996, 271(43):26469-26472.
Bringhurst et al., "Cloned, Stably Expressed Parathyroid Hormone (PTH)/PTH-Related Peptide Receptors Activate Multiple Messenger Signals and Biological Responses in LLC-PK$_1$ Kidney Cells," Endocrinology, May 1993, 132(5):2090-2098.
Broadus et al., "Parathyroid Hormone-Related Protein," The Parathyroids, J.P. Bilezikian et al., Eds., 1994, Chapter 17, 259-294.
Cross et al., Cerebrovasodilatation through selective inhibition of the enzymes carbonic Anhydrase, 1978.
Greenspan et al., "Effect of Recombinant Human Parathyroid Hormone (1-84) on Vertebral Fracture and Bone Mineral Density in Postmenopausal Women with Osteoporosis," Annals of Internal Medicine, Mar. 6, 2007, 146(5):326-339.

(Continued)

Primary Examiner — Rita Desai
(74) Attorney, Agent, or Firm — Foley & Lardner LLP

(57) ABSTRACT

The present invention provides compounds represented by formula (1) below and pharmacologically acceptable salts thereof:

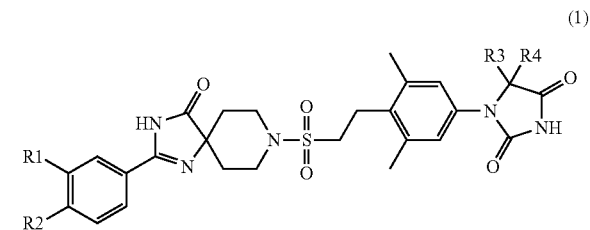

(1)

wherein $R_1$, $R_2$, $R_3$, and $R_4$ are as defined in the claims.

4 Claims, 1 Drawing Sheet

(56) References Cited

OTHER PUBLICATIONS

Hoare, Sam R.J., "Mechanisms of peptide and nonpeptide ligand binding to Class B G-protein-coupled receptors," Drug Discovery Today, Mar. 15, 2005, 10(6):417-427.
Ishihara et al., "Molecular cloning and expression of a cDNA encoding the secretin receptor," The EMBO Journal, Jul. 1991, 10(7):1635-1641.
Jelinek et al., "Expression Cloning and Signaling Properties of the Rat Glucagon Receptor," Science, Mar. 12, 1993, 259(5101):1614-1616.
Karaplis et al., "Letah skeletal dysplasia from targeted disruption of the parathyroid hormone-related peptide gene," Genes & Development, Feb. 1, 1994, 8(3):277-289.
Kolakowski, Lee F., Jr., "GCRDb: A G-Protein-Coupled Receptor Database," Receptors and Channels, 1994, 2(1):1-7.
Kronenberg et al,. "Parathyroid Hormone: Biosynthesis, Secretion, Chemistry, and Action," Handbook of Experimental Pharmacology: Physiology and Pharmacology of Bone, 1993, 507-567.
Lanske et al., "PTH/PTHrP Receptor in Early Development and Indian Hedgehog-Regulated Bone Growth," Science, Aug. 2, 1996, 273(5275):663-666.
Lin et al., "Expression Cloning of an Adenylate Cyclase-Coupled Calcitonin Receptor," Science, Nov. 15, 1991, 254(5034):1022-1024.
Mittal et al., "Newer anabolic therapies in osteoporosis," Indian J. Endocrinol. Metab., Dec. 2012, 16(Supp2):S279-S281.
Neer et al., "Effect of Parathyroid Hormone (1-34) on Fractures and Bone Mineral Density in Postmenopausal Women with Osteoporosis," New England Journal of Medicine, May 10, 2001, 344(19):1434-1441.
Patani et al., 1996, Bioisoterism.
Rejnmark et al., "PTH replacement therapy of hypoparathyroidism," Osteoporos. Int., May 2013, epub Nov. 27, 2012, 24:1529-1536.
Rickard et al., "Intermittent treatment with parathyroid hormone (PTH) as well as a non-peptide small molecule agonist of the PTH1 receptor inhibits adipocyte differentiation in human bone marrow stromal cells," Bone, Dec. 2006, epub Aug. 10, 2006, 39(6):1361-1372.

Tashjian et al.,. "Perspective: Teriparatide [Human PTH(1-34)]: 2.5 Years of Experience on the Use and Safety of the Drug for the Treatment of Osteoporosis," Journal of Bone and Mineral Research, Mar. 2006, 21(3):354-365, Epub Nov. 11, 2005.
Urena et al., "Regulation of Parathyroid Hormone (PTH)/PTH-Related Peptide Receptor Messenger Ribonucleic Acid by Glucocorticoids and PTH in ROS 17/2.8 and OK Cells," Endocrinology, Jan. 1994, 134(1):451-456.
Usdin et al., "Identification and Functional Expression of a Receptor Selectively Recognizing Parathyroid Hormone, the PTH2 Receptor," J. Biol. Chem., Jun. 30, 1995, 270(26):15455-15458.
Winer et al., "Long-Term Treatment of Hypoparathyroidism: A Randomized Controlled Study Comparing Parathyroid Hormone-(1-34) *Versus* Calcitriol and Calcium," The Journal of Clinical Endocrinology & Metabolism, Sep. 2003, 88(9):4214-4220.
Bleicher et al., "Parallel solution- and solid-phase synthesis of spirohydantoin derivatives as neurokinin-1 receptor ligands," CAplus, Chemical Abstracts, Mar. 24, 2003, 138(12):138:170128h.
Dörwald, Florencio Z., Side Reactions in Organic Synthesis, 2005, Wiley: VCH, Weinheim, p. IX of Preface.
Restriction Requirement dated Feb. 19, 2014, in U.S. Appl. No. 13/266,517.
Reply to Restriction Requirement dated Feb. 19, 2014, filed on Jul. 18, 2014, in U.S. Appl. No. 13/266,517.
Non-Final Office Action dated Jul. 28, 2014, in U.S. Appl. No. 13/266,517.
Reply to Non-Final Office Action dated Jul. 28, 2014, filed on Nov. 26, 2014, in U.S. Appl. No. 13/266,517.
Final Office Action dated Dec. 24, 2014, in U.S. Appl. No. 13/266,517.
Reply to Final Office Action dated Dec. 24, 2014, filed on Apr. 24, 2015, in U.S. Appl. No. 13/266,517.
Advisory Action dated May 14, 2015, in U.S. Appl. No. 13/266,517.
Reply to Final Office Action dated Dec. 24, 2014, and to Advisory Action dated May 14, 2015, filed on May 21, 2015, in U.S. Appl. No. 13/266,517.
Supplemental Reply to Final Office Action dated Dec. 24, 2014, and to Advisory Action dated May 14, 2015, filed on May 26, 2015, in U.S. Appl. No. 13/266,517.
Notice of Allowance and Examiner-Initiated Interview Summary dated Jun. 12, 2015, in U.S. Appl. No. 13/266,517.

\* cited by examiner

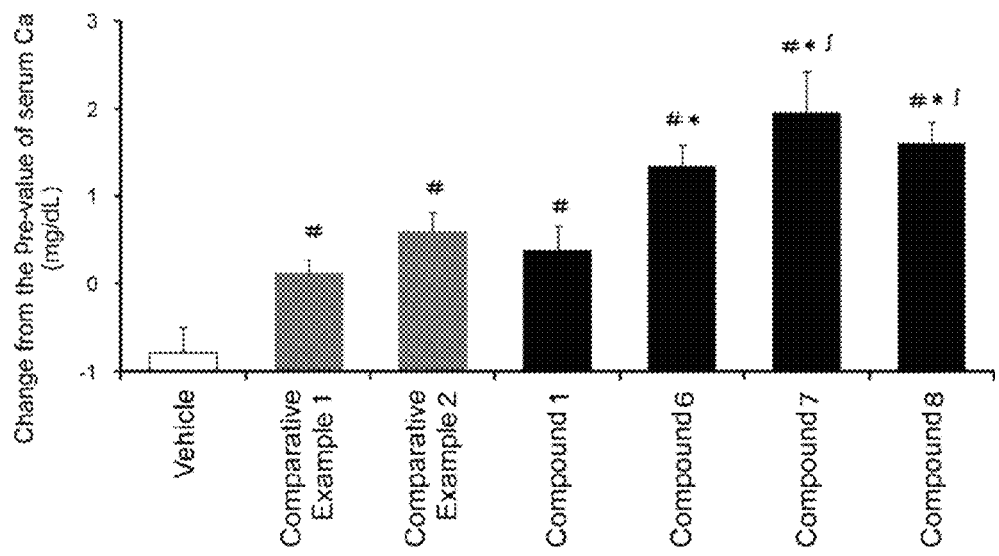

HYDANTOIN DERIVATIVE

CROSS-REFERENCE TO RELATED APPLICATIONS

This application is a National Stage application of PCT/JP2013/083022, filed Dec. 10, 2013, which claims priority from Japanese application JP 2012-269178, filed Dec. 10, 2012.

TECHNICAL FIELD

The present invention relates to pharmaceuticals comprising as an active ingredient a hydantoin derivative that has high metabolic stability and exhibits a potent PTH-like effect.

BACKGROUND ART

Parathyroid hormone (PTH) binds to the PTH1 receptor (PTH1R), which is a G protein-coupled receptor (GPCR), to activate the G protein, and then causes activation of at least one signaling cascade such as the cyclic AMP (cAMP)/protein kinase A cascade. PTH is known as a hormone that acts on target cells in the kidney and bone to regulate calcium (Ca) and phosphorus (Pi) homeostasis (Non-Patent Document 1). Serum Ca concentration level is maintained by PTH mainly through direct or indirect actions on the gastrointestinal tract, bone, and kidney. PTH promotes resorption of Ca from the renal tubules and thereby suppresses excretion of Ca in the body to the outside. It also increases the synthesis of an enzyme that converts vitamin D to active vitamin D in the kidney, and thereby contributes to the facilitation of active vitamin D-mediated Ca absorption from the gastrointestinal tract. Furthermore, PTH enhances the differentiation of osteoclasts indirectly via osteoblasts and promote Ca release from the bone. These actions of PTH are thought to occur mainly via the cyclic adenosine 3',5'-monophosphate (cAMP) elevation and/or phospholipase C (PLC) activation that occurs when PTH binds to the PTH1R.

In humans, PTH preparations [PTH (1-34) and PTH (1-84)] have a powerful osteogenic effect, and induce significant increases in bone mineral density (BMD) and bone strength. Currently, most of the osteoporosis drugs available for humans are inhibitors of bone resorption, and the only type of osteogenic drug that actively increases BMD is PTH preparations. PTH preparation is regarded as one of the most effective treatments for osteoporosis (Non-Patent Document 2); however, since it is a peptide, it needs to be administered by an invasive method. Therefore, there is an expectation for production of a pharmaceutical agent that has PTH-like effects and which can be administered non-invasively.

Hypoparathyroidism is a metabolic disease that exhibits hypocalcemia and hyperphosphatemia caused by insufficiency of PTH secreted from the parathyroid gland, and a variety of associated symptoms. Active vitamin D preparations and Ca agents are being used for the treatment of hypoparathyroidism; however, since the PTH-mediated regulatory mechanism does not work, a sufficient therapeutic effect is not obtained. Furthermore, since active vitamin D formulations enhance urinary Ca excretion, long-term therapy suggests an increased risk of nephropathy. In order to solve these problems, there is an ongoing investigation of replacement therapy that uses PTH preparations against this disease; and an attempt was made to carry out several invasive administrations per day or a continuous administration using a pump to obtain sufficient efficacy (Non-Patent Document 3). Therefore, for hypoparathyroidism treatment, generation of a pharmaceutical agent that has PTH-like effects and which can also be administered non-invasively is desirable.

Also, a pharmaceutical agent having PTH-like effects that can also be administered non-invasively is desired for treatment of diseases such as fracture, adynamic bone disease, achondroplasia, hypochondroplasia, osteomalacia, osteoarthritis, arthritis, thrombocytopenia, hyperphosphatemia, and tumoral calcinosis.

Under such circumstances, the present inventors submitted a patent application in advance based on their discovery that the compound represented by formula (A):

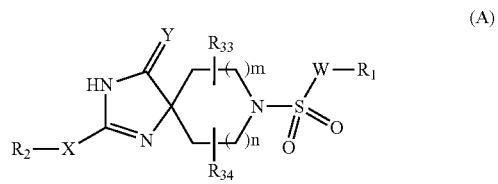

(A)

[Patent Document 1 may be referred to for W, X, Y, m, n, $R_1$, $R_2$, $R_{33}$, and $R_{34}$ in the formula] and pharmacologically acceptable salts thereof are useful as compounds having PTH-like effects, or more preferably, as a PTH1R agonist, and are useful for prevention and/or treatment of osteoporosis, fracture, osteomalacia, arthritis, thrombocytopenia, hypoparathyroidism, hyperphosphatemia, or tumoral calcinosis, or stem cell mobilization (Patent Document 1).

To produce pharmaceutical agents that have high clinical value and can be administered invasively, it is necessary to consider the in vivo kinetics such as absorption, distribution, metabolism, and excretion of the drug in addition to its direct actions on the target. To enable oral administration in particular, it is desirable to have a pharmaceutical agent having PTH-like effects which are high metabolic stability against human liver microsomes and strong human PTH1R-mediated ability of producing cAMP.

To provide a pharmaceutical agent that can be administered orally to humans, generally a method of confirming the effects of oral administration by in vivo testing that involves use of a model animal. For example, a thyroparathyroidectomized (TPTX) rat is known as an animal model for hypoparathyroidism. To find a therapeutic agent that has strong PTH-like effects and high metabolic stability, and works against hypoparathyroidism when administered orally, it is effective to use a method of finding a compound that acts on rat PTH1R and is stable to the rat's metabolic enzymes, and then examining its actions when orally administered to a TPTX rat model.

In current therapy for hypoparathyroidism, the therapeutic target range for serum Ca concentration is set to a slightly lower range than the lower limit of the normal range at 7.6 to 8.8 mg/dL (Non-Patent Document 4). Since the normal range for rat serum Ca concentration is the same level as for humans at 10 mg/dL or so, to verify the therapeutic effect, it is important to attain a serum Ca concentration in the rat model of the disease within the range from the therapeutic target range in humans (7.6-8.8 mg/dL) to the lower limit for hypercalcemia in humans (approximately 11.2 mg/dL).

PRIOR ART DOCUMENTS

Patent Documents

[Patent document 1] WO 2010/126030

Non-Patent Documents

[Non-patent document 1] Kronenberg, H. M., et al., In Handbook of Experimental Pharmacology, Mundy, G. R., and Martin, T. J., (eds), pp. 185-201, Springer-Verlag, Heidelberg (1993)
[Non-patent document 2] Tashjian and Gagel, J. Bone Miner. Res. 21:354-365 (2006)
[Non-patent document 3] Rejnmark et al., Osteoporosis Int. Published Online: 27 Nov. 2012
[Non-patent document 4] Winer K K et al., J. Clin. Endocrinol. Metab. 88(9):4214-4220 (2003)

SUMMARY OF THE INVENTION

Problems to be Solved by the Invention

An objective of the present invention is to discover compounds with strong PTH-like effects and high metabolic stability, and to provide pharmaceutical compositions comprising such compounds to enable treatment of conditions that may be treated by PTH-like actions, such as hypoparathyroidism.

Means for Solving the Problems

Under such circumstances, the present inventors continued to carry out research, and discovered that the newly discovered hydantoin derivatives of the present invention show strong cAMP-producing ability in cells expressing human PTH1R, and have high stability in human liver microsomes. The present inventors also discovered that the compounds of the present invention show strong cAMP-producing ability in cells expressing rat PTH1R, and have high stability in rat hepatocytes. Additionally, in TPTX rat models subjected to oral administration, it was newly discovered that a dose of 30 mg/kg restored the serum Ca concentration to the therapeutic target range of 7.6-8.8 mg/dL. Results obtained from these model animals suggest that the compounds represented by formula (1), which show a strong effect on human PTH1R and high stability in human liver microsomes, are useful as therapeutic agents for hypoparathyroidism.

The present invention relates to the following:
[1] A compound represented by general formula (1) below or a pharmaceutically acceptable salt thereof:

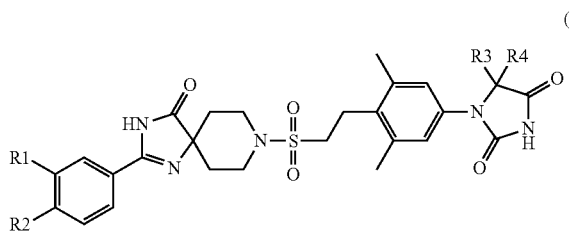

(1)

(wherein,
when R1 and R2 are not both hydrogen atoms, R1 and R2 are independently:

1) hydrogen atom;
2) halogen atom;
3) an alkyl group comprising one or two carbons that may be substituted with one to five fluorine atoms; or
4) an alkoxy group comprising one or two carbons that may be substituted with one to five fluorine atoms; or
R1 and R2 bond with each other to form a group represented by the formula below:

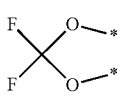

(wherein each * indicates the position of bonding with the phenyl portion); and
R3 and R4 are independently a methyl group that may be substituted with one to three fluorine atoms; or
R3 and R4, together with a bound carbon atom, form a three- to six-membered carbocyclic ring (wherein, one of the carbon atoms forming the ring may be replaced with an oxygen atom, a sulfur atom, or a methyl-substituted or unsubstituted nitrogen atom).

In the present invention, a compound in which the combination of R1 and R2 is a trifluoromethyl group and a hydrogen atom, and where R3 and R4, together with a bound carbon atom, form a cyclopentyl ring, can be excluded from the above-mentioned compounds represented by formula (1).

[2] The compound or pharmacologically acceptable salt thereof of [1], wherein R1 and R2 are selected from the combinations below:
1) R1 is a hydrogen atom or a halogen atom, and R2 is a hydrogen atom, a trifluoromethyl group, or a trifluoromethoxy group (provided that R1 and R2 are not both hydrogen atoms);
2) R1 is a trifluoromethyl group or a trifluoromethoxy group, and R2 is a hydrogen atom or a halogen atom;
3) R1 and R2 bond with each other to form a group represented by the formula below:

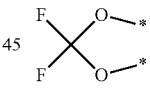

(wherein, each * indicates the position of bonding with the phenyl portion); and
R3 and R4 are methyl groups; or
R3 and R4, together with a bound carbon atom, form a ring selected from below:

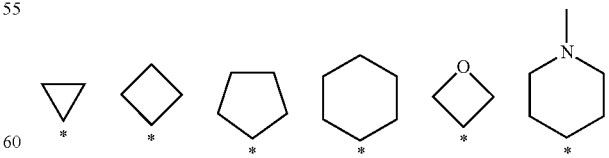

(wherein * indicates the position of bonding with the imidazolidine-2,4-dione portion).

[3] The compound or pharmacologically acceptable salt thereof of [1], wherein R1 and R2 are selected from the combinations below:

1) R1 is a trifluoromethoxy group and R2 is a fluorine atom;
2) R1 is a bromine atom and R2 is a hydrogen atom;
3) R1 is a trifluoromethoxy group and R2 is a fluorine atom;
4) R1 is a fluorine atom and R2 is a trifluoromethoxy group;
5) R1 is a trifluoromethyl group and R2 is a hydrogen atom;
6) R1 is a hydrogen atom and R2 is a trifluoromethoxy group;
7) R1 and R2 bond with each other to form a group represented by the formula below:

(wherein each * indicates the position of bonding with the phenyl portion); and
R3 and R4 are methyl groups; or
R3 and R4, together with a bound carbon atom, form a ring selected from below:

(wherein * indicates the position of bonding with the imidazolidine-2,4-dione portion).
[4] The compound or pharmacologically acceptable salt thereof of [1], wherein R3 and R4 are methyl groups.
[5] The compound or pharmacologically acceptable salt thereof of [1], wherein R3 and R4, together with a bound carbon atom, form a ring selected from below:

(wherein * indicates the position of bonding with the imidazolidine-2,4-dione portion).
[6] The compound or pharmacologically acceptable salt thereof of [1], wherein the compound is selected from the group consisting of:
1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(3-bromophenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(4-fluoro-3-(trifluoromethyl)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(3-fluoro-4-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(2,2-difluorobenzo[d][1,3]dioxol-5-yl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-5,5-dimethylimidazolidine-2,4-dione;
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione);
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione;
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione;
5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione; and
4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione.
[7] The compound or pharmacologically acceptable salt thereof of [1], wherein the compound is 1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-5,5-dimethylimidazolidine-2,4-dione
[8] The compound or pharmacologically acceptable salt thereof of [1], wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione.
[9] The compound or pharmacologically acceptable salt thereof of [1], wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione.
[10] A pharmaceutical composition, which comprises the compound or pharmacologically acceptable salt thereof of any one of [1] to [9] as an active ingredient.
[11] The pharmaceutical composition of [10], which is for use in oral administration.
[12] A pharmaceutical composition for activating intracellular cAMP response, which comprises the compound or pharmacologically acceptable salt thereof of any one of [1] to [9] as an active ingredient.
[13] A stem cell-mobilizing agent, or an agent for preventing or treating osteoporosis, fracture, adynamic bone disease, achondroplasia, hypochondroplasia, osteomalacia, osteoarthritis, arthritis, thrombocytopenia, hypoparathyroidism, hyperphosphatemia or tumoral calcinosis, which comprises the compound or pharmacologically acceptable salt thereof of any one of [1] to [9] as an active ingredient.
[14] A method for prevention or treatment of osteoporosis, fracture, adynamic bone disease, achondronplasia, hypochondroplasia, osteomalacia, osteoarthritis, arthritis, thrombocytopenia, hypoparathyroidism, hyperphosphatemia or tumoral calcinosis, or stem cell mobilization, wherein the method comprises administering a pharmaceutically effective amount of a composition comprising the compound or pharmacologically acceptable salt thereof of any of [1] to [9] to a patient in need of the prevention or treatment of the disease or stem cell mobilization.
[15] Use of the compound or pharmacologically acceptable salt thereof of any one of [1] to [9] for the production of a stem cell-mobilizing agent or an agent for preventing or treating osteoporosis, fracture, adynamic bone disease, achondroplasia, hypochondroplasia, osteomalacia, osteoarthritis, arthritis, thrombocytopenia, hypoparathyroidism, hyperphosphatemia, or tumoral calcinosis.

[16] The compound or pharmacologically acceptable salt thereof of any of [1] to [9] for treatment or prevention of osteoporosis, fracture, adynamic bone disease, achondroplasia, hypochondroplasia, osteomalacia, osteoarthritis, arthritis, thrombocytopenia, hypoparathyroidism, hyperphosphatemia, or tumoral calcinosis, or stem cell mobilization.

Furthermore the present invention provides methods for treating pathological conditions that may be treated by PTH-like actions, such as hypoparathyroidism, by administering a compound of formula (1) or a salt thereof.

Effects of the Invention

The present invention provides hydantoin derivatives with strong PTH-like effects and high metabolic stability. Use of the hydantoin derivatives enables treatment of pathological conditions caused by PTH-like actions, such as hypoparathyroidism.

BRIEF DESCRIPTION OF THE DRAWINGS

FIG. 1 depicts a graph showing the average change of level in serum Ca concentration for each compound up to 24 hours after administration, when the compound is orally administered at a dose of 30 mg/kg to a TPTX rat model.

MODE FOR CARRYING OUT THE INVENTION

The present invention relates to hydantoin derivatives and use thereof. The present inventors have synthesized a compound represented by the above formula (1) or a pharmacologically acceptable salt thereof for the first time and have found that the compound or a salt thereof is a compound having a strong parathyroid hormone (PTH)-like effect and high metabolic stability.

The "alkyl" herein refers to a monovalent group derived by removing any one hydrogen atom from an aliphatic hydrocarbon, and covers a subset of hydrocarbyl or hydrocarbon group structures not containing a heteroatom or an unsaturated carbon-carbon bond and containing hydrogen and carbon atoms in the backbone. Examples of the alkyl group include those of linear or branched structures. The alkyl group is preferably an alkyl group comprising one or two carbon atoms. The alkyl group is specifically, for example, a methyl group or an ethyl group, and is preferably a methyl group.

The term "alkoxy" as used herein refers to an oxy group to which the above-defined "alkyl" is bound, and preferably refers to an alkoxy group comprising one or two carbon atoms. Specific examples include methoxy and ethoxy groups, and a preferred example is methoxy group.

The "B optionally substituted with A" herein denotes that any hydrogen atom(s) in B may be substituted with any number of As.

In the present invention, the number of substituents is not limited unless otherwise indicated. For example, the number of substituents may be 1 to 5, 1 to 4, 1 to 3, 1 to 2, or 1.

The "halogen atom" herein refers to a fluorine atom, a chlorine atom, a bromine atom or an iodine atom.

Herein, the symbol "*" in the chemical formula refers to the position of bonding.

Compounds of the present invention represented by formula (1) has strong PTH-like effects and high metabolic stability.

The "PTH-like effect" herein refers to activity of generating intracellular cAMP (cAMP: cyclic adenosine monophosphate) by action on the PTH receptor or action on the signal transduction pathway through the PTH receptor.

In the present invention, whether there is a "strong PTH-like effect" or whether "a PTH-like effect is strong" can be confirmed by measuring the cAMP signaling activity by analyzing cAMP signaling, for example, according to the method described in J. Bone. Miner. Res. 14:11-20, 1999. Specifically, for example, according to the method described in Test Example 1, the amount of cAMP produced in cells forced to express human PTH1R is determined using a commercially available cAMP EIA kit (for example, Biotrack cAMP EIA system, GE health care) to measure the concentration of each compound at 20% cAMP signaling activity (EC20) or their concentration at 50% cAMP signaling activity (EC50), with the cAMP signaling activity obtained upon administration of 100 nM of human PTH (1-34) being defined as 100%. In the present invention, for a "strong PTH-like effect" or "a PTH-like effect is strong", for example, the EC20 value (μM) measured by the above-mentioned method is preferably 5.0 or less, more preferably 3.0 or less, and even more preferably 2.0 or less. For EC50, the value (μM) measured by the above-mentioned method is, for example, preferably 25.0 or less, more preferably 15.0 or less, and even more preferably 10.0 or less.

Whether there is "high metabolic stability" or whether the "metabolic stability is high" can be confirmed using a general measurement method. For example, liver cells, small intestinal cells, liver microsomes, small intestinal microsomes, liver S9, and such may be used for the confirmation. Specifically, for example, the stability of a compound in liver microsomes can be confirmed by taking measurements according to description in T. Kronbach et al. (Oxidation of midazolam and triazolam by human liver cytochrome P450IIIA4. Mol. Pharmacol, 1989, 36(1), 89-96). More specifically, the stability can be confirmed by following the method described in Test Example 3. In the present invention, "high metabolic stability" or "metabolic stability is high" are when the clearance (μL/min/mg) value in the metabolic stability test using human liver microsomes described in the above-mentioned Test Example is preferably 60 or less, more preferably 40 or less, and even more preferably 35 or less. Specifically, high metabolic stability can be obtained in the aforementioned formula (1), except where the combination of R1 and R2 is a trifluoromethyl group and a hydrogen atom, and R3 and R4, together with a bound carbon atom, form a cyclopentyl ring.

The compounds according to the present invention, whether free forms or pharmacologically acceptable salts, are included in the present invention. Examples of such "salts" include inorganic acid salts, organic acid salts, inorganic base salts, organic base salts and acidic or basic amino acid salts.

Preferred examples of the inorganic acid salts include hydrochlorides, hydrobromides, sulfates, nitrates and phosphates. Preferred examples of the organic acid salts include acetates, succinates, fumarates, maleates, tartrates, citrates, lactates, stearates, benzoates, methanesulfonates, benzenesulfonates, and p-toluenesulfonates.

Preferred examples of the inorganic base salts include alkali metal salts such as sodium salts and potassium salts, alkaline earth metal salts such as calcium salts and magnesium salts, aluminum salts and ammonium salts. Preferred examples of the organic base salts include diethylamine salts, diethanolamine salts, meglumine salts and N,N-dibenzylethylenediamine salts.

Preferred examples of the acidic amino acid salts include aspartates and glutamates. Preferred examples of the basic amino acid salts include arginine salts, lysine salts and ornithine salts.

The compounds of the present invention may absorb moisture, have adsorbed water or form hydrates when left in the air. Such hydrates are also included in the salts of the present invention.

Further, the compounds of the present invention may absorb certain other solvents to form solvates. Such salts are also encompassed in the present invention as salts of the compounds of the formula (1).

Herein, a structural formula of a compound may represent a certain isomer for the sake of convenience. However, the compounds of the present invention include all isomers such as geometric isomers, optical isomers based on asymmetric carbons, stereoisomers and tautomers as well as mixtures of these isomers which occur due to the structures of the compounds, without being limited to the formulas described for the sake of convenience, and may be either one of isomers or a mixture thereof. Thus, the compounds of the present invention may have an asymmetric carbon atom in the molecule and may be present as optically active forms and racemates, but the present invention is not limited to either of them and includes both of them.

The present invention includes all isotopes of the compounds represented by the formula (1). In the isotopes of the compounds of the present invention, at least one atom is replaced by an atom having the same atomic number (proton number) but having a different mass number (sum of the number of protons and the number of neutrons). Examples of the isotopes contained in the compounds of the present invention include a hydrogen atom, a carbon atom, a nitrogen atom, an oxygen atom, a phosphorus atom, a sulfur atom, a fluorine atom and a chlorine atom, including $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. In particular, radioisotopes that decay by emitting radioactivity such as $^3$H and $^{14}$C are useful in body tissue distribution tests for pharmaceuticals or compounds. Stable isotopes do not decay, are almost equal in abundance and do not emit radioactivity, and thus they can be used safely. The isotopes of the compounds of the present invention can be converted according to conventional methods by substituting a reagent containing a corresponding isotope for a reagent used for synthesis.

The compounds according to the present invention may exhibit crystalline polymorphism, but are not particularly limited to any one of these, but may be in any one of these crystal forms or exist as a mixture of two or more crystal forms.

The compounds according to the present invention include prodrugs thereof. The prodrugs are derivatives of the compounds of the present invention which have chemically or metabolically decomposable groups and are converted back to the original compounds after administration in vivo to exhibit their original efficacy, including complexes not formed with covalent bonds, and salts.

The compounds represented by the above formula (1) according to the present invention are preferably as follows.

In the formula, R1 and R2 are selected from the combinations below:

1) R1 is a hydrogen atom or a halogen atom, and R2 is a hydrogen atom, a trifluoromethyl group, or a trifluoromethoxy group (provided that R1 and R2 are not both hydrogen atoms);

2) R1 is a trifluoromethyl group or a trifluoromethoxy group, and R2 is a hydrogen atom or a halogen atom;

3) R1 and R2 bond with each other to form a group represented by the formula below:

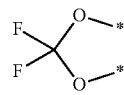

(wherein, * each indicates the position of bonding with the phenyl portion); and R3 and R4 are methyl groups; or R3 and R4, together with a bound carbon atom, form a ring selected from below:

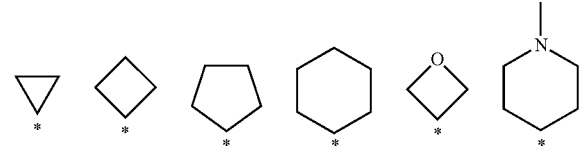

(wherein * indicates the position of bonding with the imidazolidine-2,4-dione portion).

The compounds represented by the above formula (1) according to the present invention are more preferably as follows.

In the formula, R1 and R2 are selected from the combinations below:

1) R1 is a trifluoromethoxy group and R2 is a fluorine atom;

2) R1 is a bromine atom and R2 is a hydrogen atom;

3) R1 is a trifluoromethoxy group and R2 is a fluorine atom;

4) R1 is a fluorine atom and R2 is a trifluoromethoxy group;

5) R1 is a trifluoromethyl group and R2 is a hydrogen atom;

6) R1 is a hydrogen atom and R2 is a trifluoromethoxy group;

7) R1 and R2 bond with each other to form a group represented by the formula below:

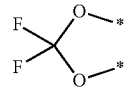

(wherein * each indicates the position of bonding with the phenyl portion); and

R3 and R4 are methyl groups; or

R3 and R4, together with a bound carbon atom, form a ring selected from below:

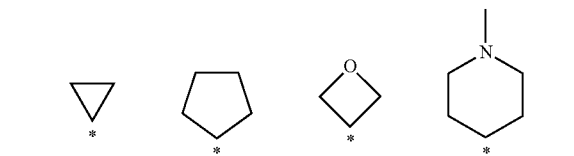

(wherein * indicates the position of bonding with the imidazolidine-2,4-dione portion).

The compounds represented by the above formula (1) according to the present invention are further preferably a compound selected from the group consisting of the following, or a pharmacologically acceptable salt thereof.

Compound 1:
1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 2:
1-(4-(2-((2-(3-bromophenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 3:
1-(4-(2-((2-(4-fluoro-3-(trifluoromethyl)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 4:
1-(4-(2-((2-(3-fluoro-4-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 5:
1-(4-(2-((2-(2,2-difluorobenzo[d][1,3]dioxol-5-yl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 6:
1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-5,5-dimethylimidazolidine-2,4-dione;

Compound 7:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione);

Compound 8:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione;

Compound 9:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione;

Compound 10:
5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione; and Compound 11:
4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione.

Of Compounds 1 to 11 above, Compounds 6, 7 and 8 are more preferred.

Such compounds represented by the above formula (1) or pharmacologically acceptable salts thereof according to the present invention are useful as compounds having a PTH-like effect, preferably PTH1R agonists, and are useful for the prevention and/or treatment of osteoporosis, fracture, adynamic bone disease, achondronplasia, hypochondroplasia, osteomalacia, osteoarthritis, arthritis, thrombocytopenia, hypoparathyroidism, hyperphosphatemia, tumoral calcinosis or the like, or stem cell mobilization.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions and the like. Commonly used excipients, binders, lubricants, colorants, correctives, and as necessary, stabilizers, emulsifiers, absorption promoters, surfactants, pH adjusters, preservatives, antioxidants and the like can be used for formulation, and they are blended with ingredients commonly used as raw materials of pharmaceutical preparations and formulated by conventional methods.

For example, oral preparations are manufactured by adding, to the compound or a pharmacologically acceptable salt thereof according to the present invention, an excipient, and as necessary, a binder, a disintegrant, a lubricant, a colorant, a corrective and the like and then formulating them into powder, fine granules, granules, tablets, coated tablets, capsules and the like by a conventional method.

Examples of these ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water.

Examples of the excipients include lactose, corn starch, white soft sugar, glucose, mannitol, sorbitol, microcrystalline cellulose and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer and meglumine.

Examples of the disintegrants include starch, agar, gelatin powder, microcrystalline cellulose, calcium carbonate, sodium bicarbonate, calcium citrate, dextrin, pectin and carboxymethylcellulose calcium.

Examples of the lubricants include magnesium stearate, talc, polyethylene glycol, silica and hydrogenated vegetable oil.

Colorants used are those approved as additives to pharmaceuticals. Correctives used are cocoa powder, peppermint camphor, empasm, mentha oil, borneol, powdered cinnamon bark and the like.

Obviously, these tablets and granules may be sugar-coated or otherwise coated appropriately as necessary. Liquid preparations such as syrups and injectable preparations are manufactured by adding a pH adjuster, a solubilizer, a tonicity adjusting agent and the like, and as necessary, a solubilizing agent, a stabilizer and the like to the compound or a pharmacologically acceptable salt thereof according to the present invention and formulating them by a conventional method.

The method of manufacturing external preparations is not limited and they can be manufactured by conventional methods. Specifically, various raw materials commonly used for pharmaceuticals, quasi drugs, cosmetics and the like can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals and purified water. Further, pH adjusters, antioxidants, chelators, preservatives and fungicides, colorants, flavors and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants and keratolytic agents may also be blended as necessary. The aforementioned base materials are added in an amount corresponding to the concentration usually chosen for the manufacture of external preparations.

The mode of administration of the compounds or salts thereof, or hydrates of the compounds or salts according to the present invention is not particularly limited, and they may be orally or parenterally administered by methods commonly used. For example, they can be formulated into preparations such as tablets, powders, granules, capsules, syrups, troches, inhalations, suppositories, injections, ointments, ophthalmic ointments, ophthalmic preparations, nasal preparations, ear preparations, cataplasms and lotions and administered.

The compounds of the present invention are particularly suitable for formulation into oral agents since they show an excellent cAMP signaling activity and have metabolic stability.

The dosage of the medicine according to the present invention can be appropriately selected depending on the severity of the symptom, the age, the sex, the body weight, the mode of administration, the type of the salt, the specific type of the disease, and the like.

Although the dosage significantly varies according to the type of the disease and the severity of the symptom of the patient, the age of the patient, the sex difference and the difference in sensitivity to drugs between the patients, and the like, the dosage is usually about 0.03 to 1000 mg, preferably 0.1 to 500 mg and more preferably 0.1 to 100 mg per day for adults and is administered divided into one to several doses a day.

In the manufacture of the compounds of the present invention represented by the above formula (1), raw material compounds and various reagents may form salts, hydrates or solvates, all vary according to the starting material, the solvent used, and the like, and are not particularly limited insofar as they do not inhibit the reaction.

The solvent used also varies according to the starting material, the reagent and the like, and is not particularly limited insofar as it does not inhibit the reaction and dissolves the starting material to a certain extent, obviously.

Various isomers (e.g., geometric isomers, optical isomers based on asymmetric carbons, rotamers, stereoisomers and tautomers) can be purified and isolated using common separation means, e.g., recrystallization, diastereomeric salt methods, enzymatic resolution methods and various chromatography methods (e.g., thin-layer chromatography, column chromatography, high performance liquid chromatography and gas chromatography).

The compounds according to the present invention obtained as free forms can be converted to salts that may be formed by the compounds or to hydrates of the compounds according to conventional methods. The compounds according to the present invention obtained as salts or hydrates of the compounds can also be converted to free forms of the compounds according to conventional methods.

The compounds according to the present invention can be isolated and purified by applying common chemical operations such as extraction, concentration, evaporation, crystallization, filtration, recrystallization and various chromatography methods.

All prior art documents cited herein are hereby incorporated by reference.

General Synthesis Methods

The compounds of the present invention can be synthesized by various methods, some of which will be described with reference to the following schemes. The schemes are illustrative and the present invention is not limited only by the chemical reactions and conditions explicitly indicated. Although some substituents are excluded in the following schemes for the sake of clarity, such exclusion is not intended to limit the disclosure of the schemes. Representative compounds of the present invention can be synthesized using appropriate intermediates, known compounds, and reagents. $R_1$, $R_2$, $R_3$ and $R_4$ in the formulas in the following general synthesis methods are as defined for $R_1$, $R_2$, $R_3$ and $R_4$ in the compounds represented by the above general formula (1) (compounds represented by formula 1 in the following general synthesis methods).

The compounds of the present invention (Formula 1) can be synthesized by the manufacturing methods (Methods A and B) shown below.

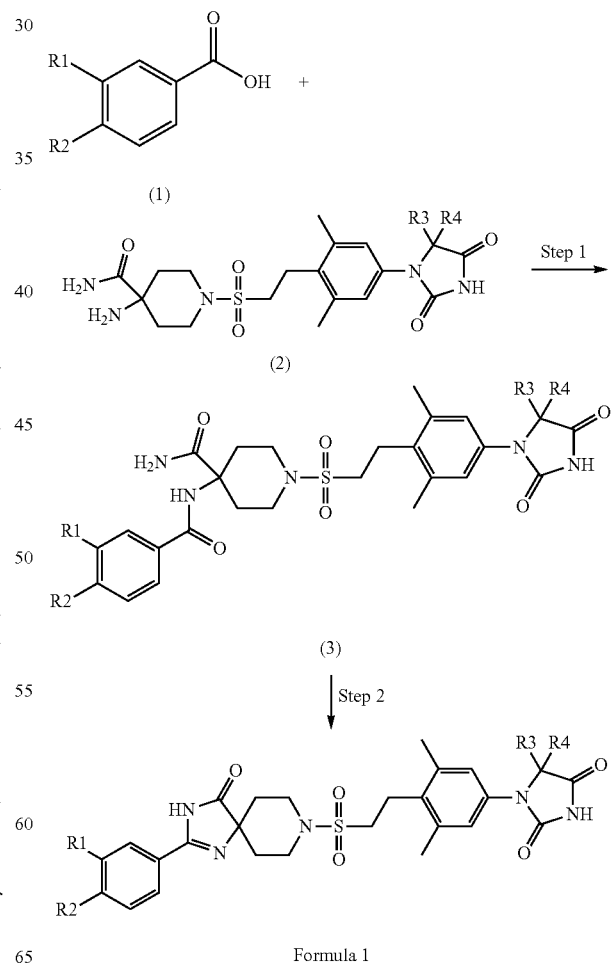

Scheme 1 (Method A)

Formula 1

Scheme 1 shows a method for obtaining a hydantoin derivative (Formula 1) by amidation of the carboxylic acid derivative (1) and the amino-amide derivative (2) to obtain the amide-amide derivative (3), and then constructing the spiroimidazolone ring by intramolecular cyclization.

Step 1 is a method of the amidation of a carboxylic acid derivative (1) and an amino-amide derivative (2). Examples of the coupling reagent include N,N'-dicyclohexylcarbodiimide (DCC), 1-ethyl-3-(3-dimethylaminopropyl)carbodiimide hydrochloride (EDC), O-(7-azabenzotriazol-1-yl)-1,1,3,3-tetramethyluronium hexafluorophosphate (HATU) and 4-(4,6-dimethoxy-1,3,5-triazin-2-yl)-4-methylmorpholinium chloride n-hydrate (DMT-MM). Examples of the base include triethylamine or N,N-diisopropylethylamine. If necessary, 4-(dimethylamino)pyridine (DMAP) may be used as a catalyst. Examples of the appropriate solvent include dichloromethane or N,N-dimethylformamide. Examples of the appropriate reaction solvent when DMT-MM is used include methanol, ethanol and acetonitrile. The reaction temperature is 0° C. to room temperature, for example, and the reaction time is 0.5 to 24 hours. The resulting amino-amide derivative (3) is isolated by a common technique and, if necessary, may be purified by crystallization or chromatography.

Step 2 is a method for the cyclization of the amide-amide derivative (3) in the presence of a suitable base such as an aqueous sodium hydroxide solution or potassium t-butoxide in a suitable solvent such as ethanol, tert-butanol, or dimethylsulfoxide. The reaction temperature is carried out, for example, under room temperature to refluxing conditions for one to 24 hours. The obtained hydantoin derivative (Formula 1) is isolated by common techniques, and when necessary, it can be purified by crystallization or chromatography.

The amino-amide derivative (2) indicated in Scheme 1 can be synthesized from the piperidine derivative (4). The synthetic method for the amino-amide derivative (2) is shown in Scheme 2.

Step 3 is a Strecker synthesis of converting a piperidinone derivative (4) to an amino-nitrile derivative (5). Specifically, this is a method of reacting a piperidinone (4) with sodium cyanide or potassium cyanide and ammonium chloride or ammonium acetate in an appropriate solvent such as methanol, ethanol or tetrahydrofuran in the presence/absence of water. The reaction temperature is room temperature to 80° C., for example, and the reaction time is 2 to 72 hours. The resulting amino-nitrile derivative (5) is isolated by a common technique and, if necessary, may be purified by crystallization or chromatography.

Step 4 is a method of converting the nitrile group to an amido group under basic hydrolysis conditions in the presence of hydrogen peroxide. This reaction can be performed with reference to Chemistry—A European Journal (2002), 8(2), 439-450, for example.

Step 5 is a method of the hydrogenation of an olefin Compound (6) in an inert solvent such as methanol, ethanol, trifluoroethanol, dimethylformamide or dimethylacetamide in the presence of a catalyst such as palladium carbon or palladium hydroxide carbon, respectively, under an $H_2$ atmosphere. The reaction temperature is room temperature to 80° C., and the reaction may be performed under pressure. The resulting amino-amide derivative (2) is isolated by a common technique and, if necessary, may be purified by crystallization or chromatography.

The piperidinone derivative (4) shown in Scheme 2 can be synthesized from a known ketal vinylsulfonyl derivative (7) and a hydantoin-arylbromide derivative (8). The synthetic method for the piperidine derivative (4) is shown in Scheme 3.

Scheme 3

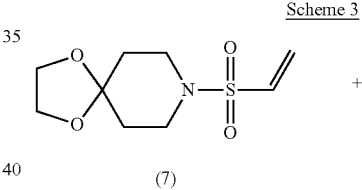

(7)

Scheme 2

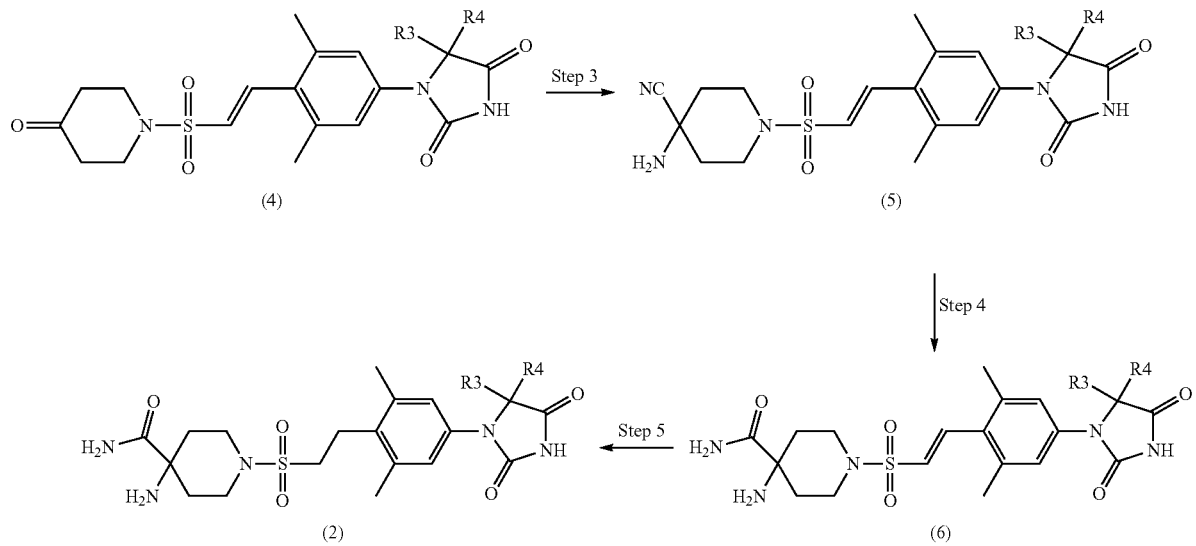

Step 6 is a method for the synthesis of a ketal-arylvinyl-sulfonyl derivative (9) by coupling the ketal vinylsulfonyl derivative (7) and the hydantoin-arylbromide derivative (8) under N₂ atmosphere in the presence of a palladium catalyst such as tris(dibenzilidineacetone)palladium(0) or bis(dibenzylidineacetone)palladium, and by adding a phosphine ligand such as tri-tert-butylphosphine tetrafluoroboric acid and a suitable base such as methyldicyclohexylamine, in a suitable solvent such as N-methyl-2-piperidone (NMP). The reaction temperature is between 90° C. and refluxing temperature. The obtained ketal-arylvinylsulfonyl derivative (9) is isolated by common techniques, and when necessary, it can be purified by crystallization or chromatography.

Step 7 is a method for the conversion of ketal of the ketal-arylvinylsulfonyl derivative (9) to ketone in a suitable solvent such as aqueous tetrahydrofuran in the presence of an acid such as hydrochloric acid. The reaction temperature is, for example, the boiling point of the solvent, and the reaction time is approximately 1 to 24 hours. The obtained piperidine derivative (4) is isolated by common techniques, and when necessary, it can be purified by crystallization or chromatography.

The hydantoin-arylbromide derivative (8) shown in Scheme 3 can be synthesized from 4-bromo-3,5-dimethylaniline (10) and the bromoacetic acid derivative (11), or from 2-bromo-5-iodo-1,3-dimethylbenzene (13) and the amino acid derivative (14). A synthetic method for the hydantoin-aryl bromide derivative (8) is shown in Scheme 4.

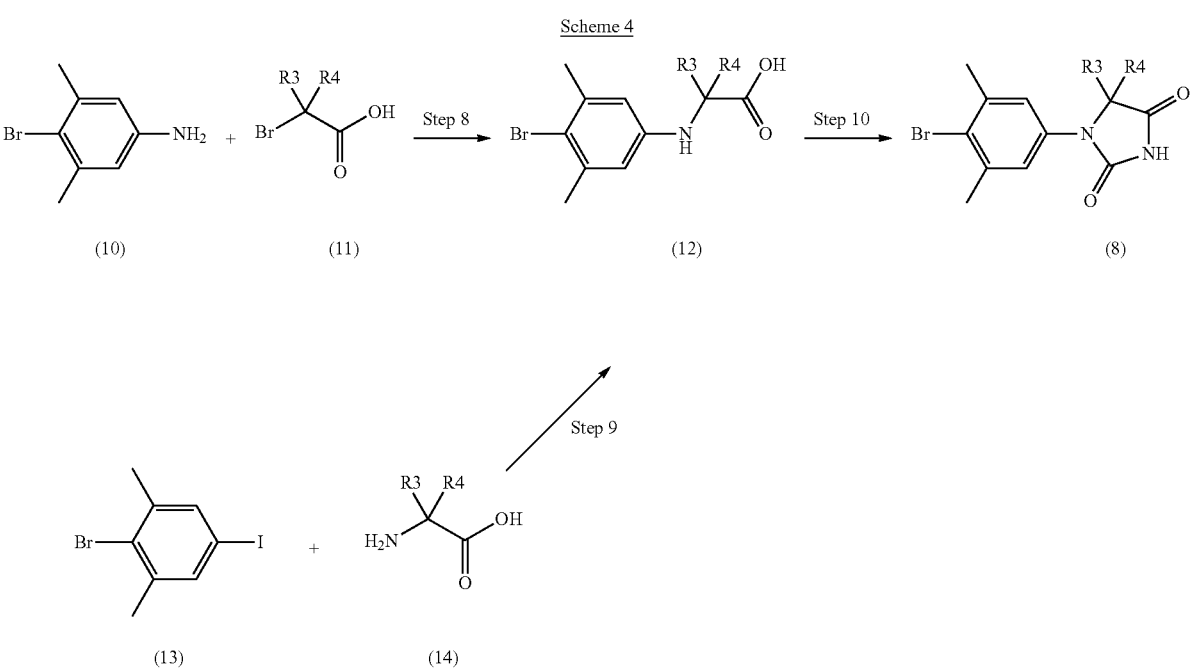

Step 8 is a method for the alkylation of 4-bromo-3,5-dimethylaniline (10) with the bromoacetic acid derivative (11) in the presence of a suitable base such as diisopropylethylamine and in a suitable solvent such as N-methyl-2-piperidone (NMP). The reaction temperature is, for example, room temperature to 100° C., and the reaction time is 1 to 24 hours. The obtained arylbromide-amino acid derivative (12) is isolated by common techniques, and when necessary, it can be purified by crystallization or chromatography.

Step 9 is a method for the synthesis of the arylbromide-amino acid derivative (12), by coupling of 2-bromo-5-iodo-1,3-dimethylbenzene (13) and the amino acid derivative (14) in the presence of a metal catalyst such as copper iodide (I). The reaction can be carried out in the presence of a suitable base such as diazabicycloundecene (DBU) and in a suitable solvent such as N,N-dimethylacetamide (DMA), at a reaction temperature of about 80° C. to 120° C. The obtained arylbromide-amino acid derivative (12) is isolated by common techniques, and when necessary, it can be purified by crystallization or chromatography.

Step 10 is a method for the synthesis of the hydantoin-arylbromide derivative (8) by reacting the arylbromide-amino acid derivative (12) with sodium cyanate under an acidic condition. The solvent is, for example, a mixed solvent such as acetic acid-dichloromethane; the reaction temperature is room temperature to 60° C.; and the reaction time is 1 to 24 hours. The obtained hydantoin-arylbromide derivative (8) may be isolated by common techniques, and when necessary, it can be purified by crystallization or chromatography.

The hydantoin-arylbromide derivative (8) shown in Scheme 3 can also be synthesized from 4-bromo-3,5-dimethylaniline (10) and a ketone derivative (15). A synthetic method for the hydantoin-arylbromide derivative (8) is shown in Scheme 5.

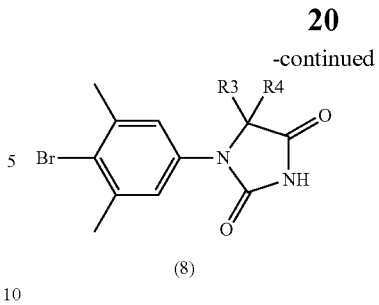

(8)

Step 11 is Strecker synthesis which directs the ketone derivative (15) to become an arylamino-nitrile derivative (16). More specifically, it is a method that reacts the ketone derivative (15) with 4-bromo-3,5-dimethylaniline (10) and trimethylsilyl cyanide in a suitable solvent such as acetic acid. The reaction temperature may be room temperature, and the reaction time is one to three hours or so. The obtained arylamino-nitrile derivative (16) is isolated by common techniques, and when necessary, it can be purified by crystallization or chromatography.

Step 12 is a method for reacting the aryl amino-nitrile derivative (16) with 2,2,2-trichloroacetylisocyanate in a suitable solvent such as dichloromethane, and then synthesizing an iminohydantoin derivative (17) by adding reagents such as methanol, water, and triethylamine and allowing them to react under heating conditions. The obtained iminohydantoin derivative (17) is isolated by common techniques, and when necessary, it can be purified by crystallization or chromatography.

Step 13 is a method for the conversion of the iminohydantoin derivative (17) into the hydantoin-arylbromide derivative (8) under an acidic condition. For example, the synthesis can be carried out in an acetic acid-water solvent with heating at approximately 65° C. for one to six hours or so. The obtained hydantoin-arylbromide derivative (8) is isolated by common techniques, and when necessary, it can be purified by crystallization or chromatography.

Scheme 6 is a method for a Heck reaction of a vinylsulfonamide derivative (18) and the hydantoin-arylbromide derivative (8) in the presence of a metal catalyst, and then the hydrogenation of olefin compound (19) to give the hydantoin derivative (Formula 1).

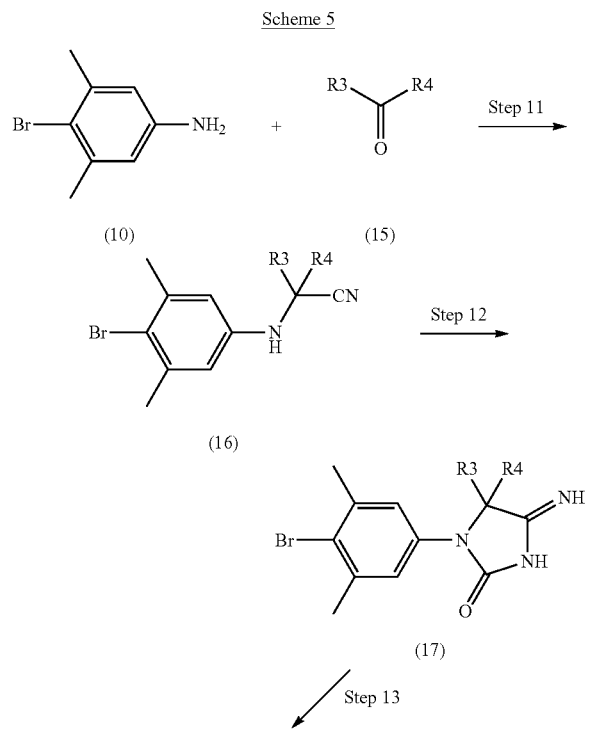

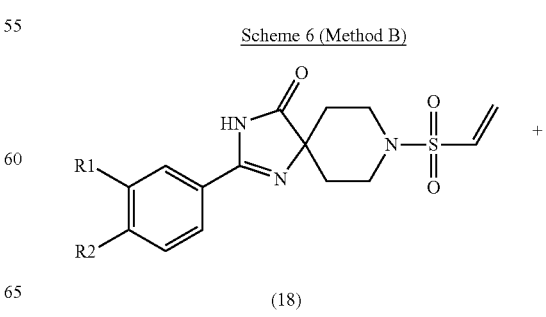

Scheme 6 (Method B)

(18)

-continued

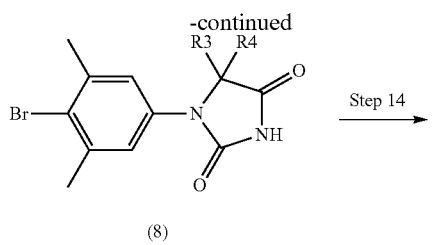

(8)

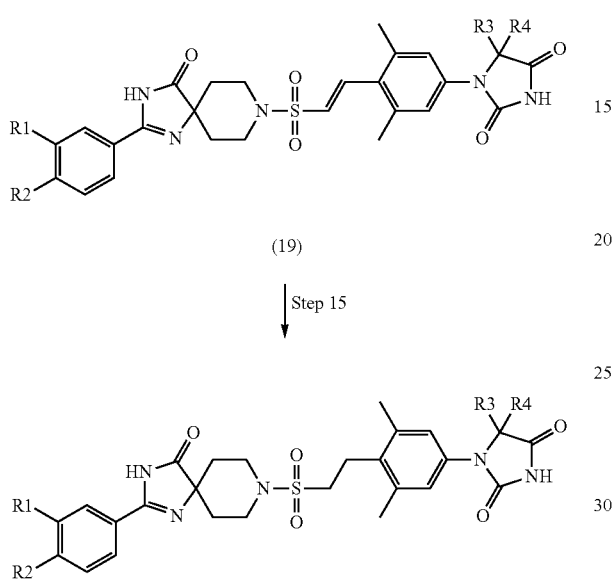

(19)

Step 15

Formula 1

The hydantoin derivative (Formula 1) can be synthesized by performing the reaction of Step 14 according to the method of Step 6 and the reaction of Step 15 according to the method of Step 5. The obtained hydantoin derivative (Formula 1) is isolated by common techniques, and when necessary, it can be purified by crystallization or chromatography.

The vinylsulfonamide derivative (18) used in Step 14 can be synthesized by referring to Schemes 2, 3, and 12 of WO2010/126030(A1).

All prior art documents cited in this specification are incorporated herein by reference.

EXAMPLES

The content of the present invention will be described in more detail by the following examples and test example; however, the present invention is not limited to the content of the examples and test example. All starting materials and reagents were obtained from commercial suppliers or synthesized using known methods. $^1$H-NMR spectra were measured using Mercury300 (manufactured by Varian), ECP-400 (manufactured by JEOL) or 400-MR (manufactured by Varian) with or without Me$_4$Si as the internal standard (s=singlet, d=doublet, t=triplet, brs=broad singlet, m=multiplet). Mass spectrometry measurement was performed using a mass spectrometer, ZQ2000 (manufactured by Waters), SQD (manufactured by Waters) or 2020 (manufactured by Shimazu).

Example 1

1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione (Compound 1)

Reaction (1-1)

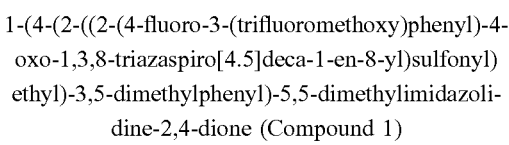

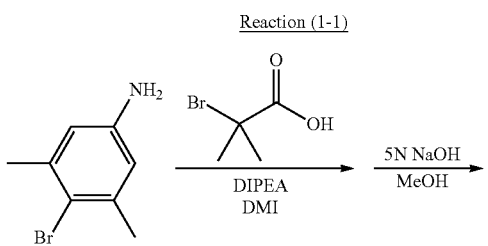

To a solution of 4-bromo-3,5-dimethylaniline (3.47 g, 17.4 mmol) and diisopropylethylamine (5.3 mL, 30.4 mmol) in DMI (13 mL), 2-bromoisobutyric acid (3.86 g, 23.1 mmol) was added at room temperature. The mixture was stirred at 100° C. for one hour. And then 2-bromoisobutyrate (496 mg, 2.97 mmol) and diisopropylethylamine (0.8 mL, 4.59 mmol) was added and the mixture was stirred at 100° C. for one hour.

Methanol (52 mL) and a 5 N aqueous sodium hydroxide solution (52 mL, 260 mmol) were added to the reaction mixture at room temperature, and then this mixture was stirred at 75° C. for 1.5 hours. The reaction mixture was cooled, followed by addition of water and adjustment of the pH to 5 using a 1 N aqueous potassium hydrogen sulfate solution, and then extracted using ethyl acetate. The organic layer was washed with water, then dried over anhydrous magnesium sulfate, and concentrated to yield 2-((4-bromo- 3,5-dimethylphenyl)amino)-2-methyl propanoic acid as a crude product (5.79 g).

MS (ESI) m/z=286, 288 (M+H)+

(Reaction 1-2)

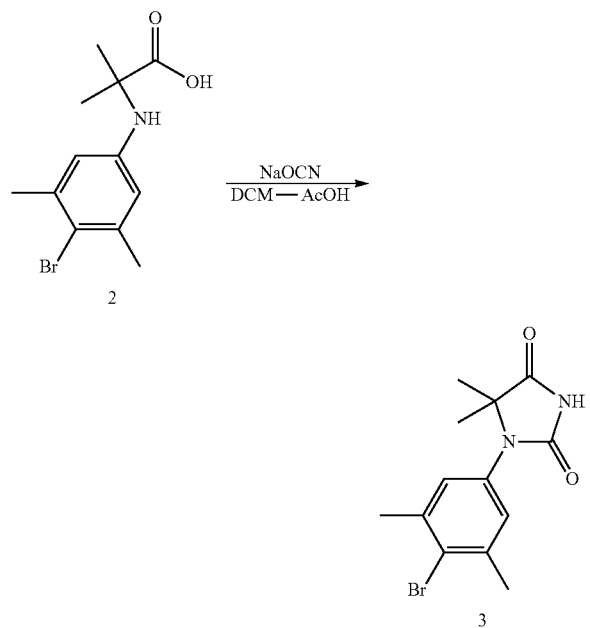

To a mixture of 2-((4-bromo-3,5-dimethylphenyl)amino)-2-methyl propanoic acid (5.79 g of the compound obtained from Reaction 1-1) in dichloromethane (62 mL) and acetic acid (62 mL), sodium cyanate (5.03 g, 59.8 mmol) was added at room temperature. The mixture was stirred at room temperature for three hours. A saturated solution of sodium hydrogen carbonate (400 mL) was added to adjust the pH to 7-8 using a 5 N aqueous sodium hydroxide, and this mixture was extracted with ethyl acetate. The organic layer was dried over anhydrous magnesium sulfate, and then concentrated under reduced pressure. The obtained solid was washed sequentially with ethyl acetate-hexane and then with dichloromethane-hexane to obtain 1-(4-bromo-3,5-dimethylphenyl)-5,5-dimethylimidazolidine-2,4-dione (3.80 g, 66%).

MS (ESI) m/z=311, 313 (M+H)+

(Reaction 1-3)

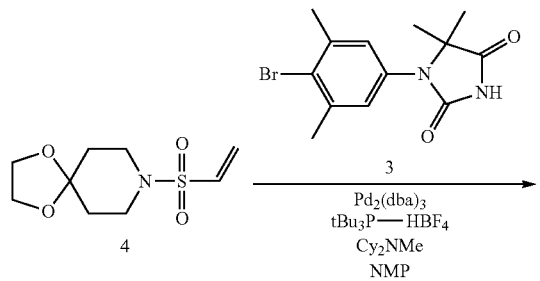

A mixture of 8-(vinylsulfonyl)-1,4-dioxa-8-azaspiro[4.5]decane (431 mg, 1.85 mmol), 1-(4-bromo-3,5-dimethylphenyl)-5,5-dimethylimidazolidine-2,4-dione (575 mg, 1.85 mmol), tris(dibenzylidineacetone)palladium(0) (508 mg, 0.55 mmol), tri-tert-butylphosphine tetrafluoroboric acid (165 mg, 0.55 mmol), and methyldicyclohexylamine (2.1 mL, 9.25 mmol) in N-methyl-2-pyrrolidone (18.5 mL) was stirred under nitrogen atmosphere at 110° C. for two hours. The reaction mixture was cooled, quenched with water, and then extracted with ethyl acetate. The organic layer was washed with water and brine, dried over anhydrous magnesium sulfate, and then concentrated under reduced pressure. The residue was purified by amino-silica gel column chromatography (dichloromethane-methanol) to afford (E)-1-(4-(2-(1,4-dioxa-8-azaspiro[4.5]decan-8-ylsulfonyl)vinyl)-3,5-dimethylphenyl)-5,5-dimeth ylimidazolidine-2,4-dione (584 mg, 68%).

MS (ESI) m/z=464 (M+H)+

(Reaction 1-4)

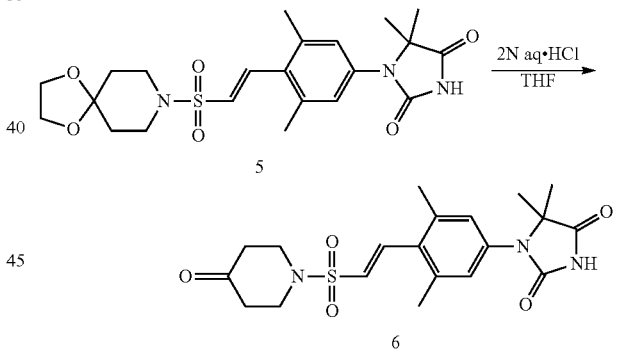

To a solution of (E)-1-(4-(2-(1,4-dioxa-8-azaspiro[4.5]decan-8-ylsulfonyl)vinyl)-3,5-dimethylphenyl)-5,5-dimeth ylimidazolidine-2,4-dione (1.2 g, 2.58 mmol) in tetrahydrofuran (26 mL), a 2 N aqueous hydrochloric acid solution (26 mL, 52 mmol) was added dropwise over ten minutes. The mixture was stirred at 60° C. for two hours. The reaction mixture was cooled, followed by adjustment of its pH to 7 using a 2 N aqueous sodium hydroxide solution, and this mixture was extracted with ethyl acetate. The organic layer was washed with brine, dried over anhydrous magnesium sulfate, and then concentrated under reduced pressure. The residue was purified by silica gel column chromatography (dichloromethane-ethyl acetate) to afford (E)-1-(3,5-dimethyl-4-(2-((4-oxopiperidin-1-yl)sulfonyl)vinyl)phenyl)-5,5-dimethylimidazolidine-2,4-dione (998 mg, 92%).

MS (ESI) m/z=420 (M+H)+

(Reaction 1-5)

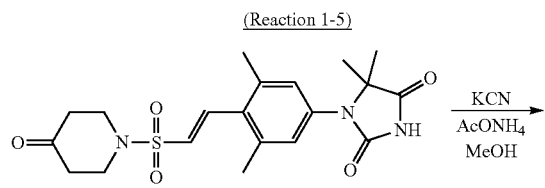

(Reaction 1-6)

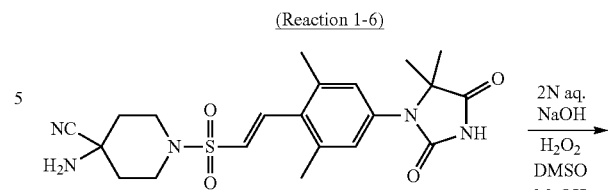

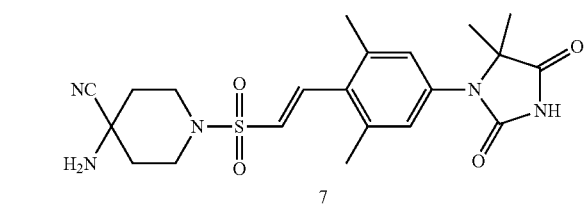

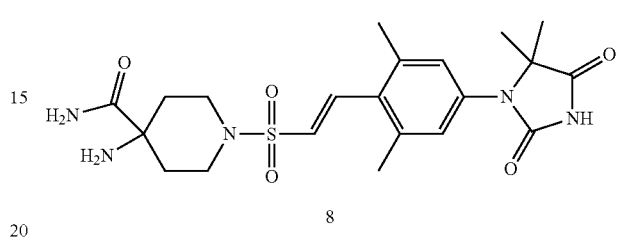

To a solution of (E)-1-(3,5-dimethyl-4-(2-((4-oxopiperidin-1-yl)sulfonyl)vinyl)phenyl)-5,5-dimethylimidazolidine-2,4-dione (994 mg, 2.37 mmol) in methanol (24 mL), potassium cyanide (188 mg, 2.84 mmol) and ammonium acetate (237 mg, 3.08 mmol) were added at room temperature. The mixture was stirred at 60-70° C. for three hours. The reaction mixture was cooled, concentrated under reduced pressure, and then diluted with ethyl acetate. The organic layer was washed with water and brine, dried over anhydrous magnesium sulfate, and then concentrated under reduced pressure. The residue was purified by silica gel column chromatography (dichloromethane-ethyl acetate) to afford (E)-4-amino-1-((4-(5,5-dimethyl-2,4-dioxoimidazolidin-1-yl)-2,6-dimethylstyryl)sulfonyl)piperidine-4-carbonitrile (681 mg, 68%).

$^1$H-NMR (300 MHz, DMSO-$d_6$) δ: 1.3 (6H, s), 1.7 (2H, m), 2.0 (2H, m), 2.3 (6H, s), 2.7 (2H, s), 2.9 (2H, m), 3.4 (2H, m), 6.9 (1H, d, J=15.9 Hz), 7.1 (2H, s), 7.4 (1H, d, J=15.9 Hz), 11.2 (1H, brs)

To a solution of (E)-4-amino-1-((4-(5,5-dimethyl-2,4-dioxoimidazolidin-1-yl)-2,6-dimethylstyryl)sulfonyl)piperidine-4-carbonitrile (675 mg, 1.50 mmol) in methanol (7.5 mL) and dimethylsulfoxide (0.195 mL) at room temperature, a 2 N aqueous sodium hydroxide solution (1.6 ml, 1.6 mmol) was added and then a 30% aqueous hydrogen peroxide solution (0.2 mL, 1.95 mmol) were slowly added dropwise. The mixture was stirred at room temperature for one hour. Ethyl acetate, hexane, and a saturated aqueous ammonium chloride solution were added to the reaction mixture. The solid was collected by filtration, washed, and dried to afford (E)-4-amino-1-((4-(5,5-dimethyl-2,4-dioxoimidazolidine-1-yl)-2,6-dimethylstyryl)sulfonyl)piperidine-4-carboxamide (498 mg, 72%).

MS (ESI) m/z=464 (M+H)+

(Reaction 1-7)

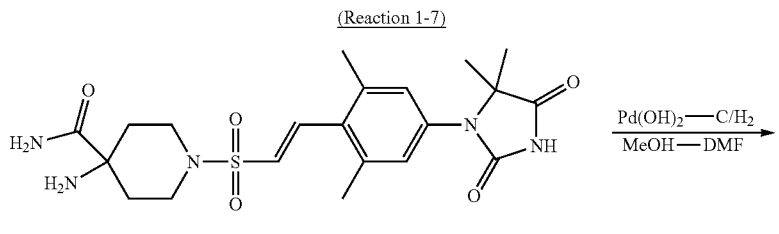

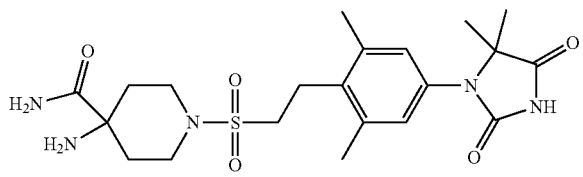

A mixture of (E)-4-amino-1-((4-(5,5-dimethyl-2,4-dioxoimidazolidine-1-yl)-2,6-dimethylstyryl)sulfonyl)piperidine-4-carboxamide (1.3 g, 2.8 mmol) and palladium hydroxide on carbon (20% Pd) (wetted with approximately 50% water) (1.3 g) in methanol (21 mL) and dimethylformamide (7 mL) was stirred under hydrogen atmosphere at room temperature for four hours. The reaction mixture was filtered and washed, and then the filtrate was concentrated under reduced pressure to afford 4-amino-1-((4-(5,5-dimethyl-2,4-dioxoimidazolidin-1-yl)-2,6-dimethylphenethyl)sulfonyl)piperidin-4-carboxamide (998 mg, 77%).

MS (ESI) m/z=466 (M+H)+

(Reaction 1-8)

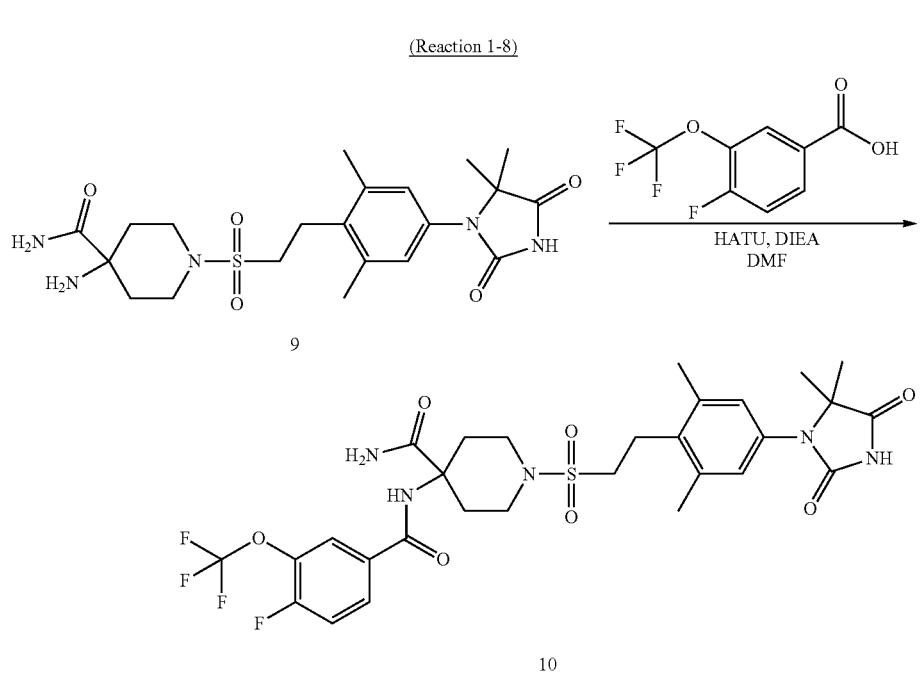

To a solution of 4-amino-1-((4-(5,5-dimethyl-2,4-dioxoimidazolidin-1-yl)-2,6-dimethylphenethyl)sulfonyl)piperidin-4-carboxamide (120 mg, 0.258 mmol), 4-fluoro-3-(trifluoromethoxy)benzoic acid (69 mg, 0.309 mmol), and diisopropylethylamine (0.09 ml, 0.516 mmol) in dimethylformamide (2.5 mL), O-(7-azabenzotriazol-1-yl)-1,1,3,3-tetramethyluroniumhexafluorophosphate (HATU) (118 mg, 0.309 mmol) was added. The mixture was stirred at room temperature for 1.5 hours. The reaction mixture was quenched with water, and then extracted with dichloromethane. The organic layer was washed with brine, washed with anhydrous sodium sulfate, and then concentrated under reduced pressure to afford 1-((4-(5,5-dimethyl-2,4-dioxoimidazolidin-1-yl)-2,6-dimethylphenethyl)sulfonyl)-4-(4-fluoro-3-(trifluoromethoxy)benzamide)piperidine-4-carboxamide (150 mg, 67%).

MS (ESI) m/z=672 (M+H)+

(Reaction 1-9)

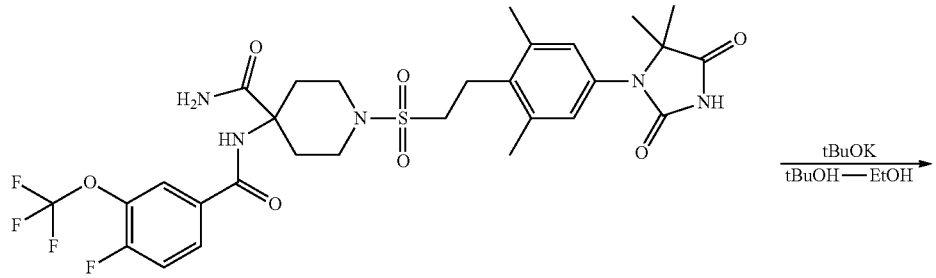

-continued

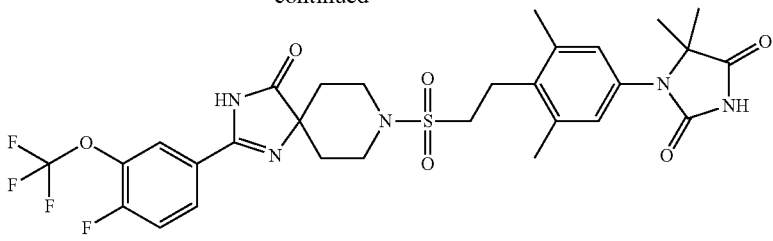

Compound 1

To a mixed solution of 1-((4-(5,5-dimethyl-2,4-dioxoimidazolidin-1-yl)-2,6-dimethylphenethyl)sulfonyl)-4-(4-fluoro-3-(trifluoromethoxy)benzamide)piperidine-4-carboxamide (150 mg, 0.223 mmol) in tert-butanol (2.5 mL) and ethanol (2.5 mL), potassium tert-butoxide (75 mg, 0.670 mmol) was added at 0° C. The mixture was stirred under nitrogen atmosphere at 50° C. for 1.5 hours. The reaction mixture was cooled, diluted with water, quenched with a saturated aqueous ammonium chloride solution, and then extracted with dichloromethane. The organic layer was washed with water and brine, dried over anhydrous sodium sulfate, and then concentrated under reduced pressure. The obtained residue was purified by silica gel column chromatography (dichloromethane-methanol) to afford 1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione 118 mg, 81%).

MS (ESI) m/z=654 (M+H)+. $^1$H-NMR (400 MHz, CD$_3$OD) δ: 1.40 (6H, s), 1.71-1.80 (2H, m), 2.00-2.08 (2H, m), 2.43 (6H, s), 3.22 (4H, s), 3.47-3.57 (2H, m), 3.80-3.88 (2H, m), 7.01 (2H, s), 7.50-7.57 (1H, m), 7.97-8.04 (1H, m), 8.05-8.12 (1H, m)

The following compounds of the Examples were synthesized by operations similar to those of Reactions 1-8 and 1-9 in Example 1, using appropriate carboxylic acid starting materials, reagents, and solvents.
(Compound 2-5)

TABLE 1

| Compound | Carboxylic acid starting material | Structural formula of compound | Analytical data |
|---|---|---|---|
| 2 | ![3-bromobenzoic acid] | ![structure 2] | MS(ESI) m/z = 630, 632 (M + H)+, $^1$H-NMR (400 MHz, DMSO-d$_6$) δ: 1.30 (6H, s), 1.56-1.63 (2H, m), 1.80-1.90 (2H, m), 2.37 (6H, s), 3.00-3.08 (2H, m), 3.23-3.30 (2H, m), 3.32-3.41 (2H, m), 3.67-3.73 (2H, m), 7.00 (2H, s), 7.50 (1H, dd, J = 8.8 Hz), 7.77-7.82 (1H, m), 7.95-8.00 (1H, m), 8.13-8.20 (1H, m), 11.10 (1H, brs), 11.70 (1H, brs) |
| 3 | ![3-trifluoromethyl-4-fluorobenzoic acid] | ![structure 3] | MS(ESI) m/z = 538 (M + H)+, $^1$H-NMR (400 MHz, CDCl$_3$) δ: 1.47 (6H, s), 1.70-1.78 (2H, m), 2.09-2.18 (2H, m), 2.40 (6H, s), 3.00-3.08 (2H, m), 3.20-3.28 (2H, m), 3.44-3.54(2H, m), 3.80-3.88 (2H, m), 6.94 (2H, s), 7.34 (1H, t, J = 9.6 Hz), 8.02 (1H, brs), 8.08-8.13 (1H, m), 8.20-8.24 (1H, m), 10.10 (1H, brs) |
| 4 | ![3-fluoro-4-trifluoromethoxybenzoic acid] | ![structure 4] | MS(ESI) m/z = 654 (M + H)+, $^1$H-NMR (400 MHz, DMSO-d$_6$) δ: 1.30 (6H, s), 1.58-1.64 (2H, m), 1.81-1.91 (2H, m), 2.37 (6H, s), 3.00-3.08 (2H, m), 3.22-3.31 (2H, m), 3.32-3.42 (2H, m), 3.68-3.73 (2H, m), 7.00 (2H, s), 7.76-7.82 (1H, m), 7.95 (1H, d, J = 9.6 Hz), 8.05 (1H, dd, J = 9.6, 2 Hz), 11.09 (1H, s), 11.79 (1H, s) |

TABLE 1-continued

| Compound | Carboxylic acid starting material | Structural formula of compound | Analytical data |
|---|---|---|---|
| 5 | | | MS(ESI) m/z = 632 (M + H)+, $^1$H-NMR (400 MHz, CDCl$_3$) δ: 1.47 (6H, s), 1.65-1.73 (2H, m), 2.11-2.20 (2H, m), 2.39 (6H, s), 2.98-3.04 (2H, m), 3.18-3.25 (2H, m), 3.40-3.52 (2H, m), 3.82-3.90 (2H, m), 6.94 (2H, s), 7.17 (1H, d, J = 8.4 Hz), 7.63 (1H, d, J = 3.4 Hz), 7.75 (1H, s), 8.49 (1H, brs), 10.46 (1H, brs) |

Example 2

1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione (Compound 6)

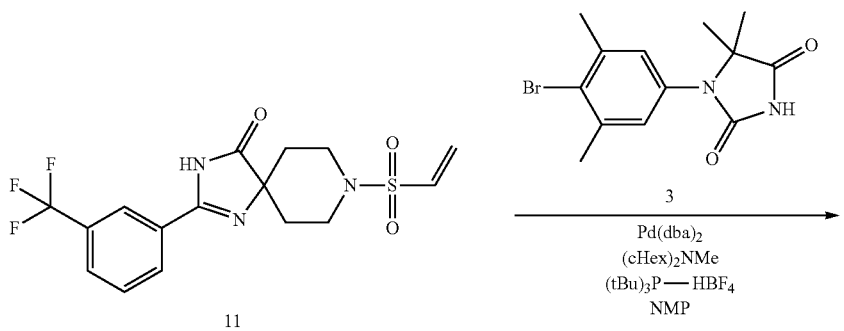

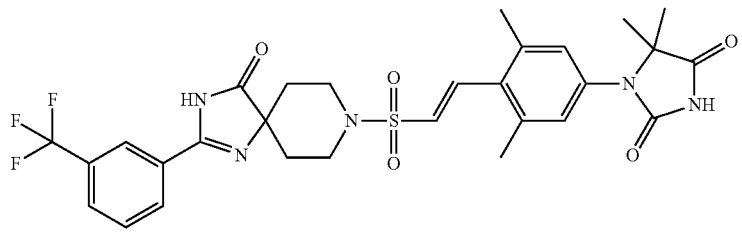

A mixture of 2-(3-(trifluoromethyl)phenyl)-8-(vinylsulfonyl)-1,3,8-triazaspiro[4.5]deca-1-en-4-one (150 mg, 0.387 mmol) synthesized according to the method described in Schemes 2, 3, and 12 of WO2010/126030(A1), 1-(4-bromo-3,5-dimethylphenyl)-5,5-dimethylimidazolidine-2,4-dione (169 mg, 0.542 mmol), bis(dibenzylidineacetone) palladium (45 mg, 0.077 mmol), tri-tert-butylphosphine tetrafluoroboric acid (22 mg, 0.077 mmol), and methyldicyclohexylamine (0.123 mL, 0.581 mmol) in N-methyl-2-pyrrolidone (0.97 mL) was stirred at 100° C. for one hour under nitrogen atmosphere. The reaction mixture was cooled, quenched with water, and then extracted with ethyl acetate. The organic layer was washed with water and brine, dried over anhydrous sodium sulfate, and then concentrated under reduced pressure. The obtained residue was purified by silica gel column chromatography (ethyl acetate-hexane) to afford (E)-1-(3,5-dimethyl-4-(2-((4-oxo-2-(3-(trifluoromethyl)phenyl)-1,3,8-triazaspiro[4.5]deca-1-en-8-yl)sulfonyl)vinyl)phenyl)-5,5-dimethylimidazolidine-2,4-dione (197 mg, 82%).

MS (ESI) m/z=618 (M+H)+

(Reaction 2-2)

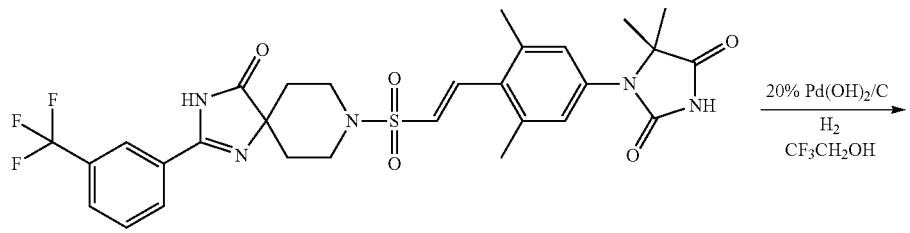

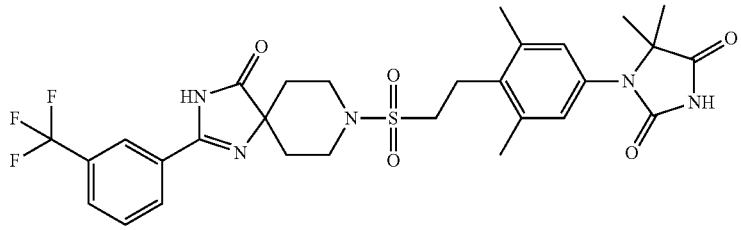

Compound 6

A mixture of (E)-1-(3,5-dimethyl-4-(2-((4-oxo-2-(3-(trifluoromethyl)phenyl)-1,3,8-triazaspiro[4.5]deca-1-en-8-yl)sulfonyl)vinyl)phenyl)-5,5-dimethylimidazolidine-2,4-dione (195 mg, 0.316 mmol) and palladium hydroxide/carbon (20% Pd) (wetted with approximately 50% water) (195 mg, 0.139 mmol) in 2,2,2-trifluoroethanol (6 mL) was stirred at room temperature for 14 hours under hydrogen atmosphere. The mixture was filtered, and the filtrate was concentrated under reduced pressure. The obtained residue was purified by silica gel column chromatography (ethyl acetate-hexane) to afford 1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-5,5-dimethylimidazolidine-2,4-dione (121 mg, 62%).

MS (ESI) m/z=620 (M+H)+. $^1$H-NMR (400 MHz, CD$_3$OD) δ: 1.40 (6H, s), 1.72-1.81 (2H, m), 2.00-2.10 (2H, m), 2.44 (6H, s), 3.22 (4H, s), 3.50-3.58 (2H, m), 3.80-3.88 (2H, m), 7.01 (2H, s), 7.72-7.79 (1H, m), 7.88-7.94 (1H, m), 8.16-8.23 (1H, m), 8.31 (1H, s)

Example 3

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione (Compound 7)

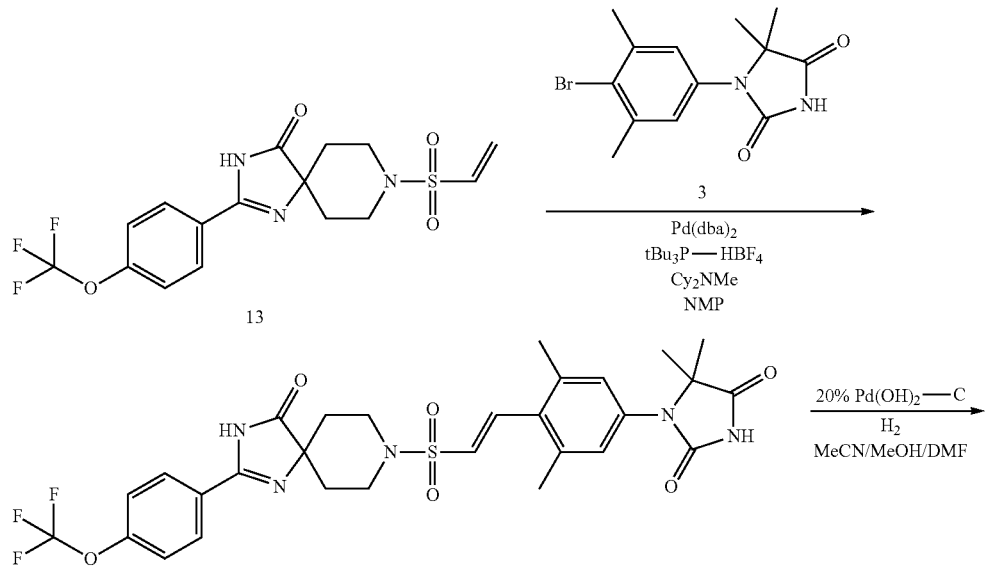

-continued

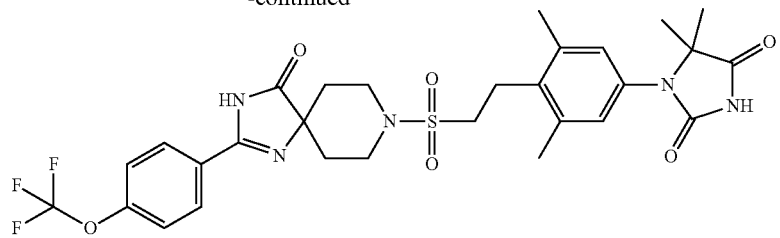

Compound 7

With the use of appropriate starting materials and solvents, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione (Compound 7) was synthesized by operations similar to those described in Example 2.

MS (ESI) m/z=636 (M+H)+. $^1$H-NMR (400 MHz, CDCl$_3$) δ: 1.47 (6H, s), 1.70-1.78 (2H, m), 2.10-2.19 (2H, m), 2.40 (6H, s), 3.00-3.07 (2H, m), 3.19-3.25 (2H, m), 3.45-3.53 (2H, m), 3.81-3.88 (2H, m), 6.94 (2H, s), 7.35 (2H, d, J=8.0 Hz), 7.73 (1H, brs), 7.93 (2H, d, J=8.0 Hz), 9.37 (1H, brs)

Example 4

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione (Compound 8)

(Reaction 4-1)

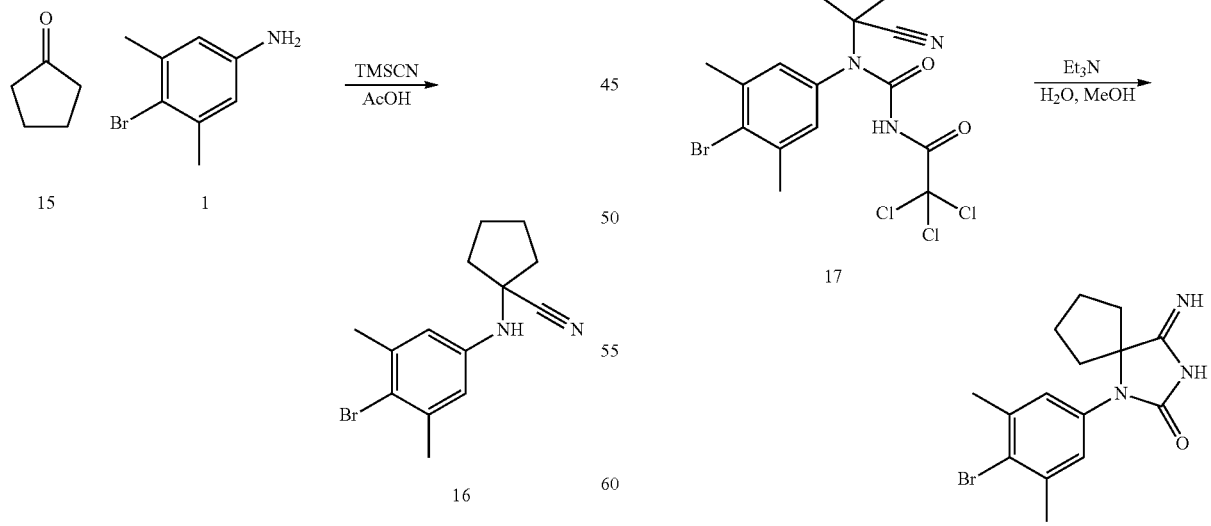

To a mixture of cyclopentanone (42 mg, 0.500 mmol) and 4-bromo-3,5-dimethylaniline (100 mg, 0.500 mmol) in acetic acid (0.5 mL), trimethylsilyl cyanide (0.063 ml, 0.500 mmol) was added at room temperature. The mixture was stirred at room temperature for 1.5 hours under nitrogen atmosphere. The reaction mixture was quenched with 28% aqueous ammonia (1 mL), diluted with water and extracted with dichloromethane. The organic layer was washed with water and brine, dried over anhydrous sodium sulfate, and then concentrated under reduced pressure to afford 1-((4-bromo-3,5-dimethylphenyl)amino)cyclopentanecarbonitrile as a crude product (152 mg).

$^1$H-NMR (400 MHz, CDCl$_3$) δ: 1.83-1.92 (4H, m), 2.07-2.15 (2H, m), 2.33-2.42 (2H, m), 2.37 (6H, m), 3.71 (1H, brs), 6.56 (2H, s)

(Reaction 4-2)

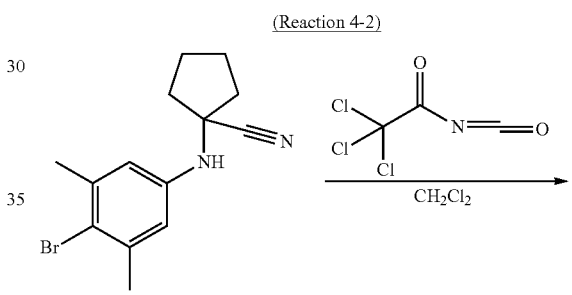

To a solution of 1-((4-bromo-3,5-dimethylphenyl)amino)cyclopentanecarbonitrile (145 mg, 0.495 mmol) in dichloromethane (5 mL), 2,2,2-trichloroactylisocyanate (0.070 mL, 0.593 mmol) was added at room temperature. The mixture was stirred at room temperature for one hour under nitrogen atmosphere.

Triethylamine (0.103 mL, 0.742 mmol), water (0.045 mL), and methanol (0.10 mL) were added and the mixture was refluxed for 1.5 hours under nitrogen atmosphere. The reaction mixture was cooled, followed by dilution with water and adjustment of its pH to 5 using a 1 N aqueous hydrochloric acid solution, and then extracted with dichloromethane. The organic layer was washed with water and brine, dried over anhydrous sodium sulfate, and then concentrated under reduced pressure to afford 1-(4-bromo-3,5-dimethylphenyl)-4-imino-1,3-diazaspiro[4.4]nonan-2-one as a crude product.

MS (ESI) m/z=336, 338 (M+H)+

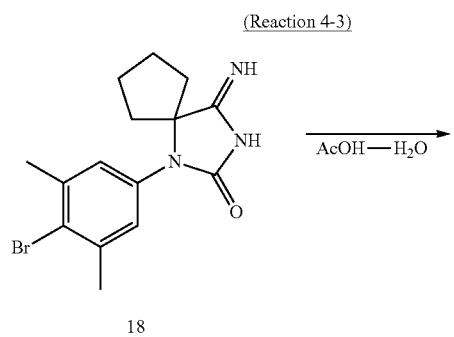

(Reaction 4-3)

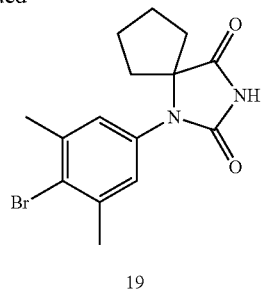

19

A mixture of 1-(4-bromo-3,5-dimethylphenyl)-4-imino-1,3-diazaspiro[4.4]nonan-2-one (the crude product obtained in the previous reaction) in acetic acid (1.0 mL) and water (0.25 mL) was stirred for 1.5 hours at 65° C. under nitrogen atmosphere. After further addition of acetic acid (1.0 mL) and water (0.25 mL), the mixture was stirred for 17 hours at 65° C. under nitrogen atmosphere. The reaction mixture was cooled, followed by dilution with water and adjustment of its pH to 8 using a saturated aqueous sodium hydrogen carbonate solution, and extracted with ethyl acetate. The organic layer was washed with water and brine, dried over anhydrous sodium sulfate, and then concentrated under reduced pressure. The residue was purified by silica gel column chromatography (ethyl acetate-hexane) to afford 1-(4-bromo-3,5-dimethylphenyl)-1,3-diazaspiro[4.4]nonane-2,4-dione (121 mg).

MS (ESI) m/z=337, 339 (M+H)+

(Reaction 4-4)

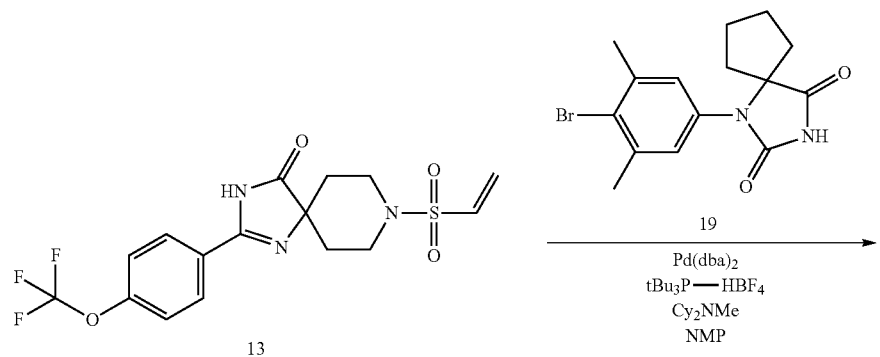

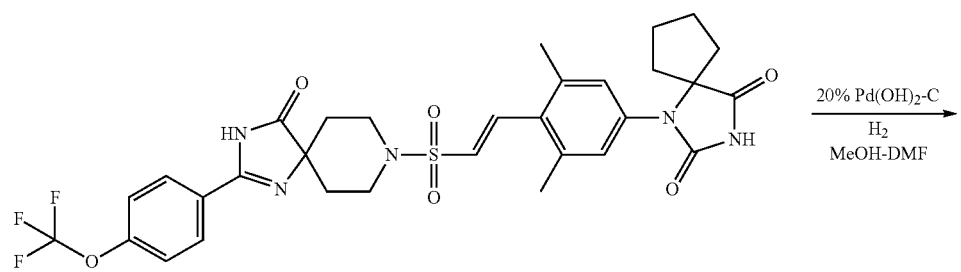

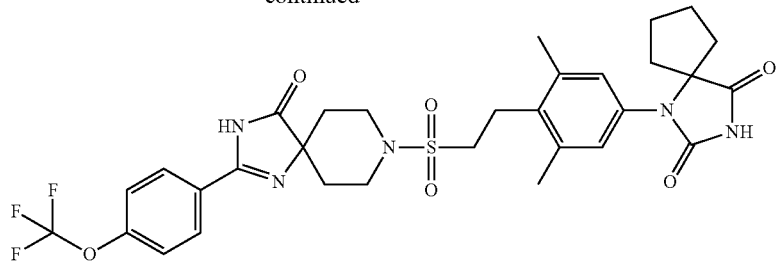

Compound 8

With the use of appropriate starting materials and solvents, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione (Compound 8) was obtained by operations similar to those described in Example 2.

MS (ESI) m/z=662 (M+H)+. $^1$H-NMR (400 MHz, DMSO-$d_6$) δ: 1.36-1.44 (2H, m), 1.60-1.70 (4H. m), 1.82-1.91 (2H, m), 1.91-2.06 (4H, m), 2.38 (6H, s), 3.01-3.09 (2H, m), 3.22-3.30 (2H, m), 3.30-3.42 (2H, m), 3.70-3.77 (2H, m), 7.03 (2H, s), 7.57 (2H, d, J=8.4 Hz), 8.14 (2H, d, J=8.4 Hz)

Example 5

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione (Compound 9)

(Reaction 5-1)

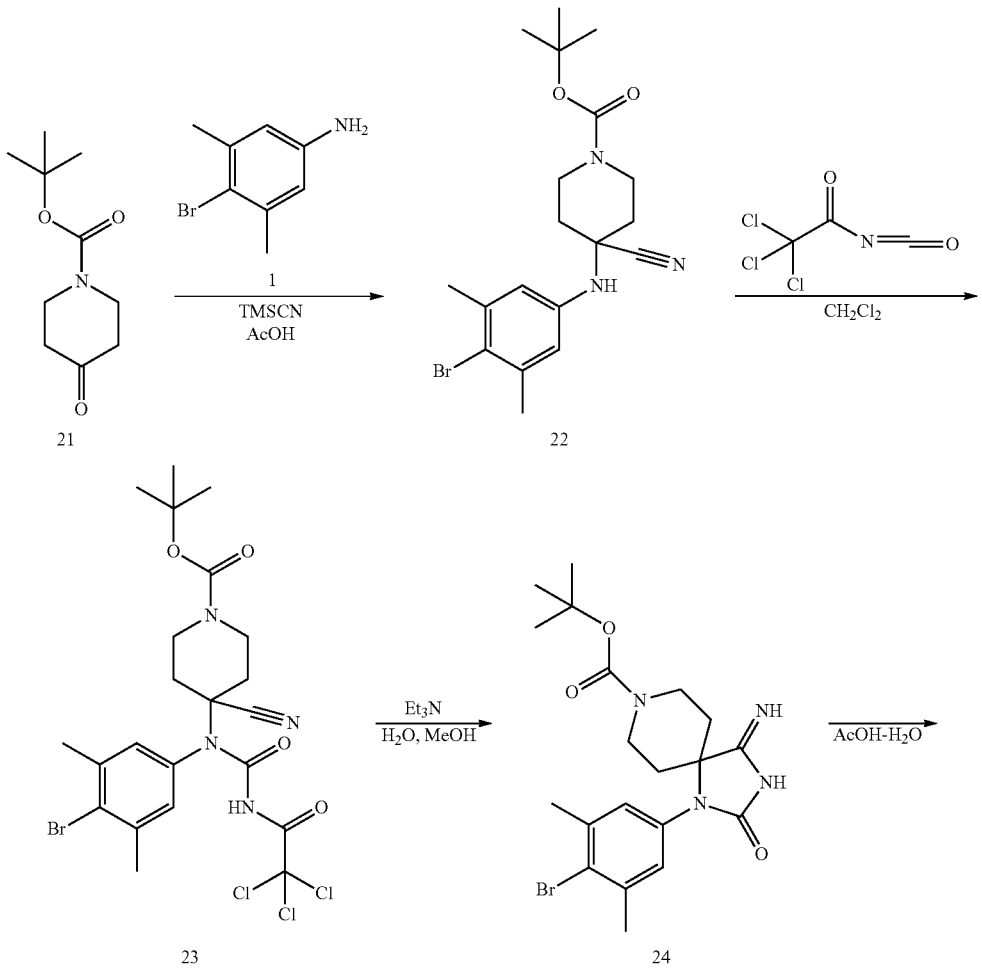

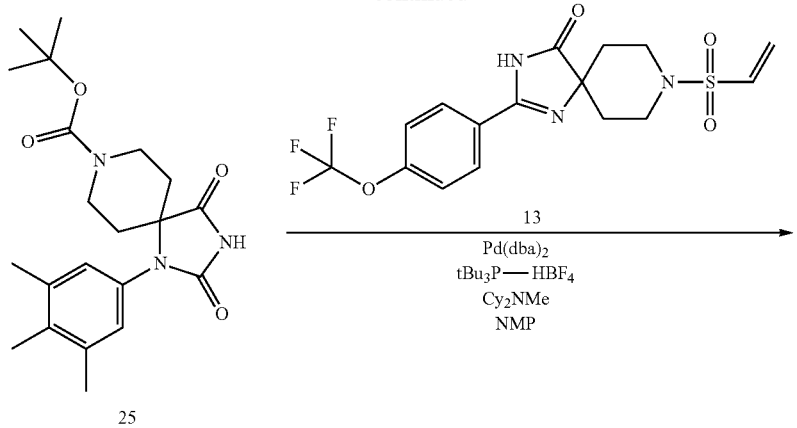
25
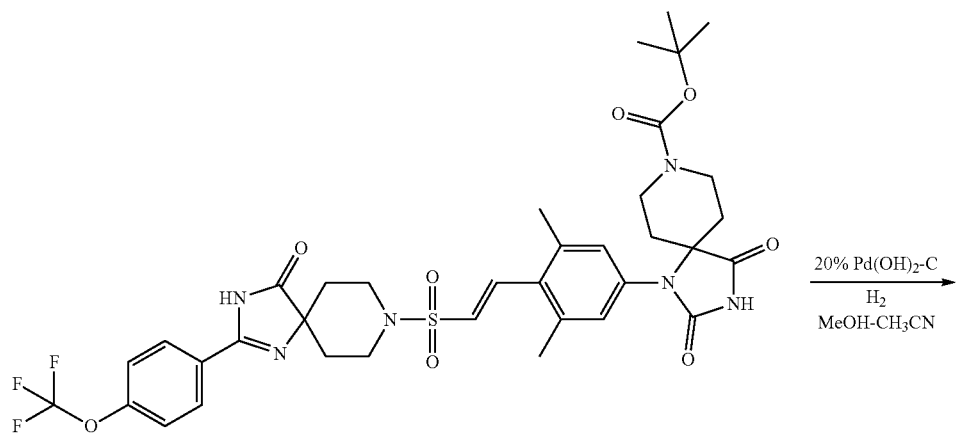
26
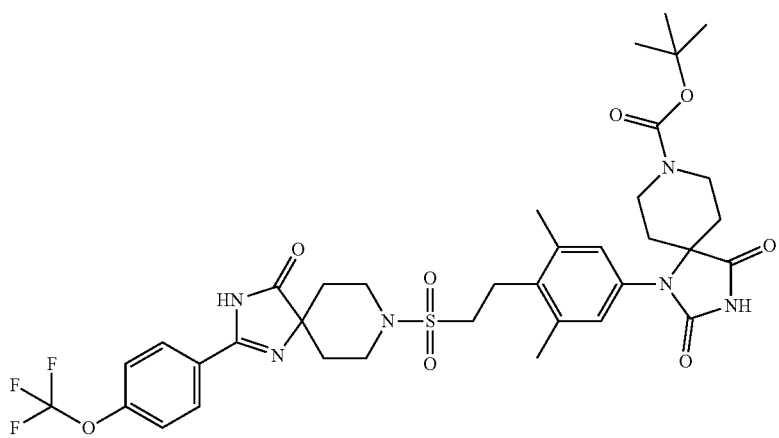
27
With the use of 4-oxopiperidine-1-carboxylic acid tert-butyl ester as a starting material, and the use of an appropriate solvent, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2,4-dioxo-1,3,8-triazaspiro[4.5]decan-8-carboxylic acid tert-butyl ester was obtained by operations similar to those described in Example 4.
MS (ESI) m/z=777 (M+H)+.

(Reaction 5-2)

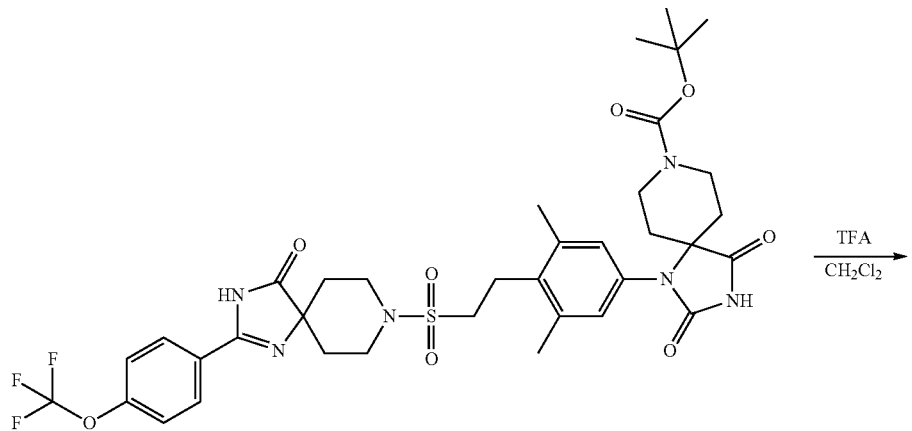

27

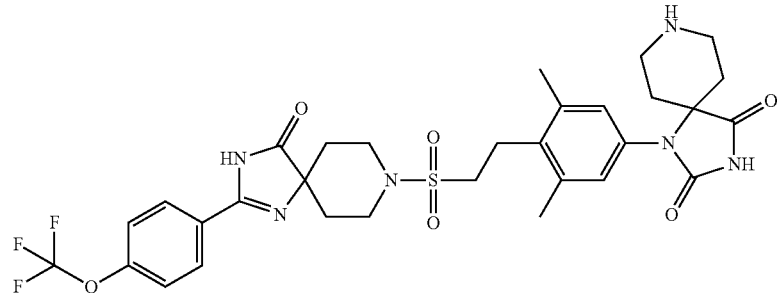

28

To a mixed solution of 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2,4-dioxo-1,3,8-triazaspiro[4.5]decane-8-carboxylic acid tert-butyl ester (11.7 mg, 0.015 mmol) in dichloromethane (0.13 mL), trifluoroacetic acid (0.05 mL, 0.673 mmol) was added at room temperature. The mixture was placed under a stream of nitrogen, and stirred at room temperature for one hour. The reaction mixture was concentrated under reduced pressure to obtain 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3,8-triazaspiro[4.5]decane-2,4-dione 2 trifluoroacetic acid salt (13.6 mg).

MS (ESI) m/z=677 (M+H)+.

(Reaction 5-3)

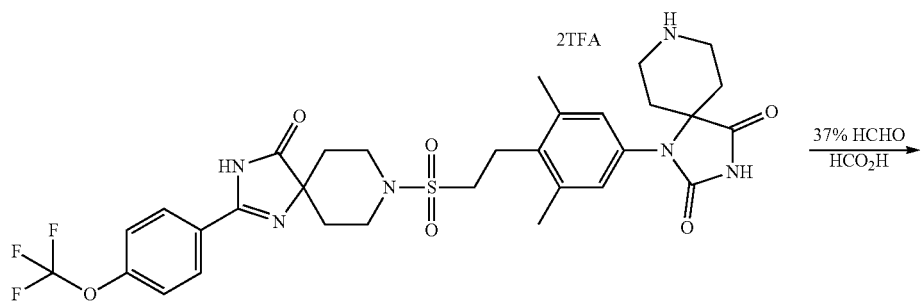

28

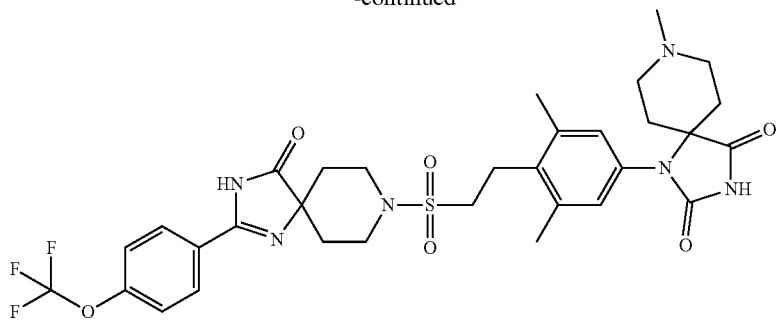

Compound 9

To a mixture of 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3,8-triazaspiro[4.5]decan-2,4-dione 2 trifluoroacetic acid salt (21.1 mg, 0.022 mmol) and formic acid (0.033 mL), a 37% aqueous formaldehyde solution (0.055 mL) was added. The mixture was placed under a stream of nitrogen, and stirred for three hours while heating at 80° C. The reaction mixture was concentrated, and the resulting residue was diluted with ethyl acetate. The organic layer was washed with a diluted aqueous sodium hydroxide solution, dried over anhydrous magnesium sulfate, and then concentrated under reduced pressure. The obtained residue was subjected to column chromatography (dichloromethane-methanol) for purification to obtain 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl-8-methyl-1,3,8-triazaspiro[4.5]decane-2,4-dione (4.5 mg, 30%).

MS (ESI) m/z=691 (M+H)+. $^1$H-NMR (400 MHz, CD$_3$OD) δ: 1.76-1.84 (2H, m), 1.92-2.02 (2H, m), 2.02-2.12 (4H, m), 2.38 (3H, s), 2.46 (6H, s), 2.81-2.88 (2H, m), 2.92-3.02 (2H, m), 3.23 (4H, s), 3.51-3.60 (2H, m), 3.72-3.80 (2H, m), 7.01 (2H, s), 7.48 (2H, d, J=8.0 Hz), 8.10 (2H, d, J=8.0 Hz)

Example 6

5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione (Compound 10)

(Reaction 6)

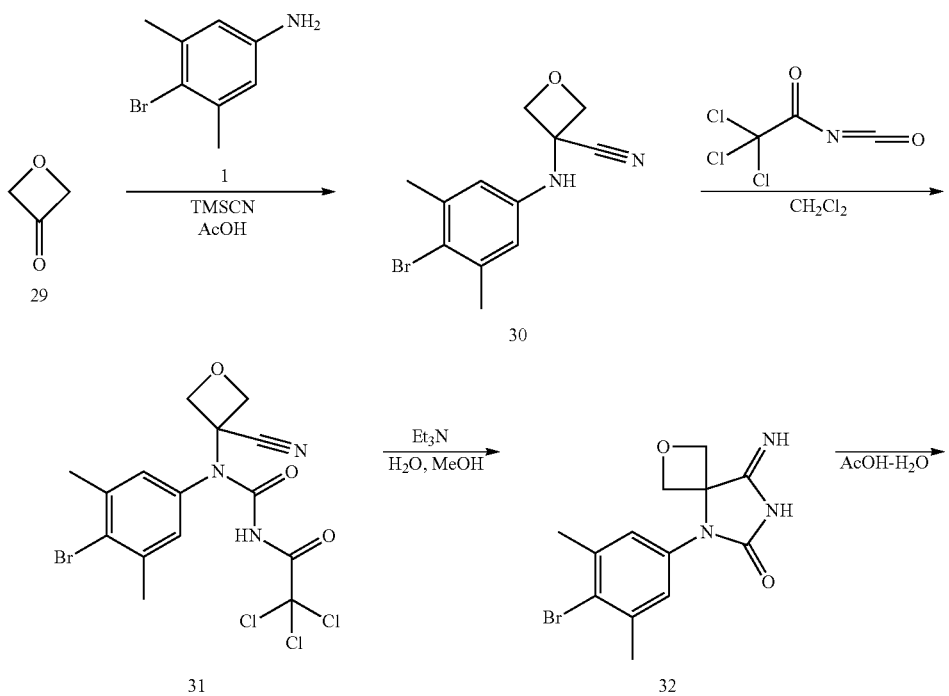

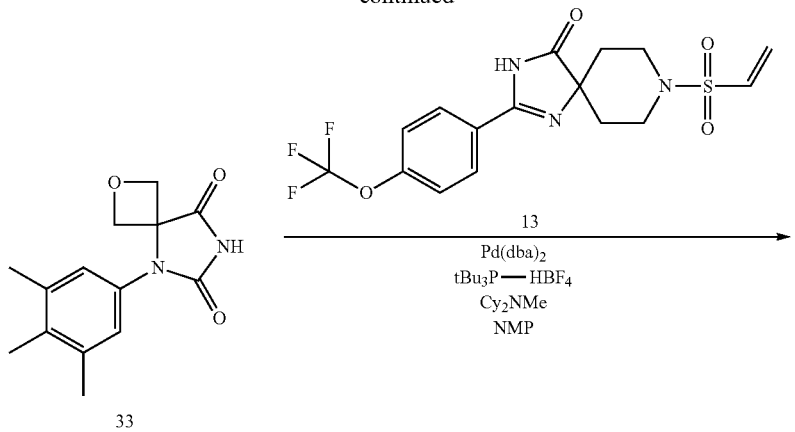
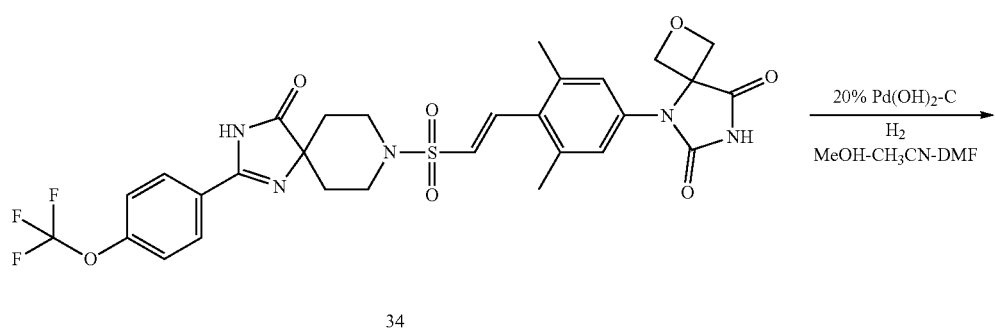
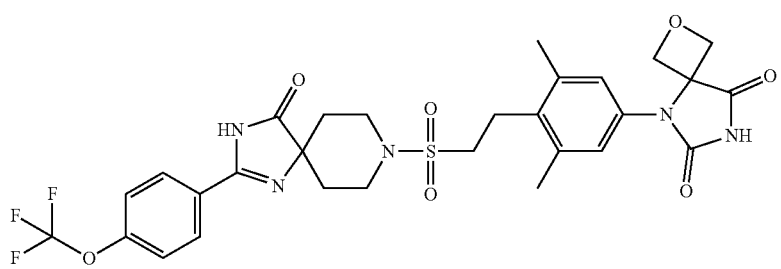
Compound 10
With the use of oxetane-3-one as a starting material, and the use of appropriate solvents, 5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione was obtained by operations similar to those of Example 4.
MS (ESI) m/z=650 (M+H)+. $^1$H-NMR (400 MHz, CDCl$_3$) δ: 1.69-1.77 (2H, m), 2.12-2.22 (2H, m), 2.45 (6H, s), 3.03-3.11 (2H, m), 3.22-3.29 (2H, m), 3.46-3.53 (2H, m), 3.84-3.91 (2H, m), 4.86 (2H, d, J=7.2 Hz), 5.03 (2H, d, J=7.2 Hz), 7.07 (2H, s), 7.35 (2H, d, J=8.4 Hz), 7.98 (2H, d, J=8.4 Hz), 8.56 (1H, s), 10.34 (1H, s)

Example 7

4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione (Compound 11)

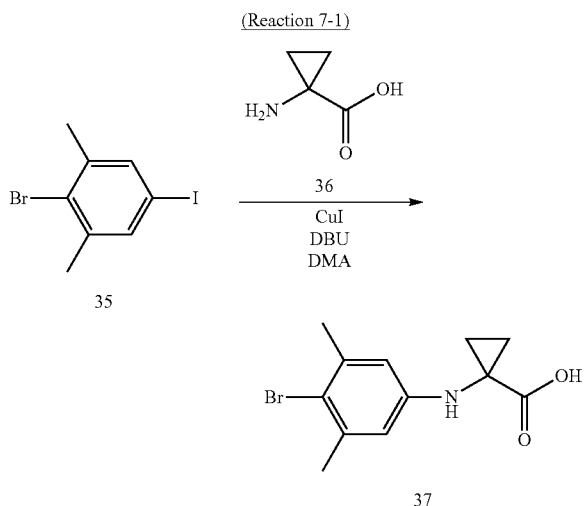

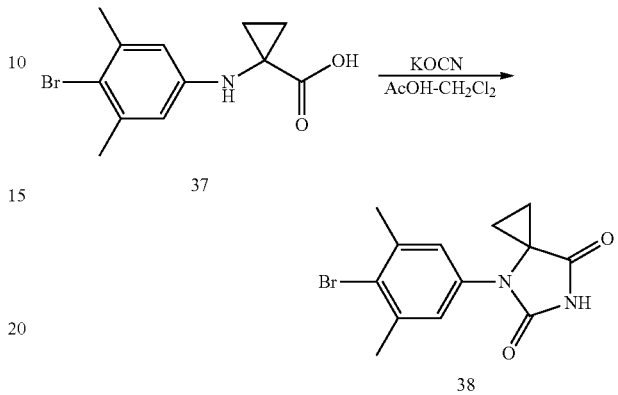

A mixture of 2-bromo-5-iodo-1,3-dimethylbenzene (300 mg, 0.965 mmol), 1-aminocyclopropane carboxylic acid (195 mg, 1.93 mmol), copper iodide (I) (37 mg, 0.194 mmol), and diazabicycloundecene (0.50 mL, 3.35 mmol) in dimethylacetamide (2.6 mL) was stirred at 120° C. for three hours under nitrogen atmosphere. The reaction mixture was purified by silica gel column chromatography (Wakosil C18, acetonitrile-water (0.1% formic acid)) to afford 1-((4-bromo-3,5-dimethylphenyl)amino)cyclopropane carboxylic acid (219 mg, 80%).

MS (ESI) m/z=284, 286 (M+H)+.

To a mixture of 1-((4-bromo-3,5-dimethylphenyl)amino)cyclopropane carboxylic acid (198 mg, 0.697 mmol) in acetic acid (3 mL) and dichloromethane (1.5 mL), potassium cyanate (424 mg, 5.23 mmol) was added at room temperature. The mixture was stirred at room temperature for one hour, and then stirred at 60° C. for two hours. A saturated aqueous sodium hydrogen carbonate solution was added to adjust pH to 8, and this mixture was extracted with ethyl acetate. The organic layer was washed with water and brine, dried over anhydrous sodium sulfate, and then concentrated under reduced pressure. The residue was purified by silica gel column chromatography (ethyl acetate-hexane) to afford 4-(4-bromo-3,5-dimethylphenyl)-4,6-diazaspiro[2.4]heptane-5,7-dione (49 mg, 23%).

MS (ESI) m/z=309, 311 (M+H)+.

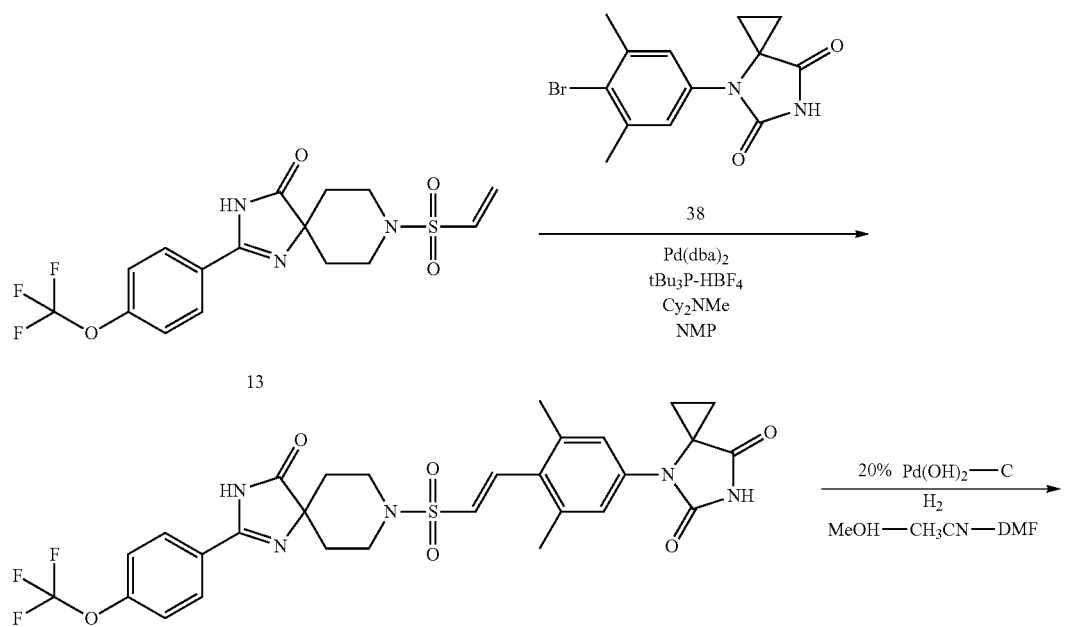

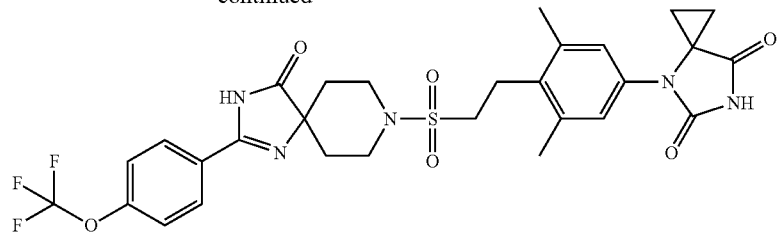

Compound 11

With the use of appropriate starting materials and solvents, 4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione (Compound 11) was obtained by operations similar to those of Example 2.

MS (ESI) m/z=634 (M+H)+. $^1$H-NMR (400 MHz, DMSO-d$_6$) δ: 0.99-1.03 (2H, m), 1.19-1.27 (4H, m), 1.58-1.64 (2H, m), 1.81-1.90 (2H, m), 2.35 (6H, s), 2.99-3.04 (2H, m), 3.22-3.29 (2H, m), 3.67-3.73 (2H, m), 6.95 (2H, s), 7.56 (2H, d, J=8.4 Hz), 8.12 (2H, d, J=8.4 Hz)

Example 8

1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-1,3-diazaspiro[4.4]nonane-2,4-dione (Compound 12)

(Reaction 8)

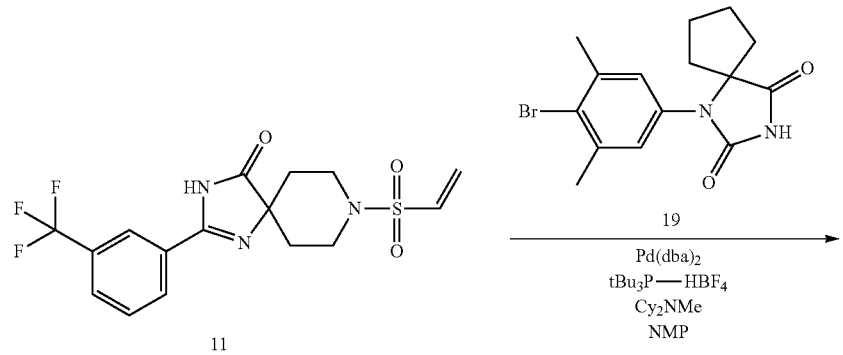

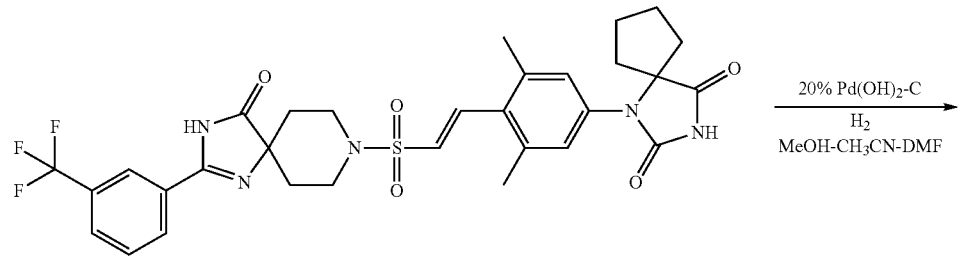

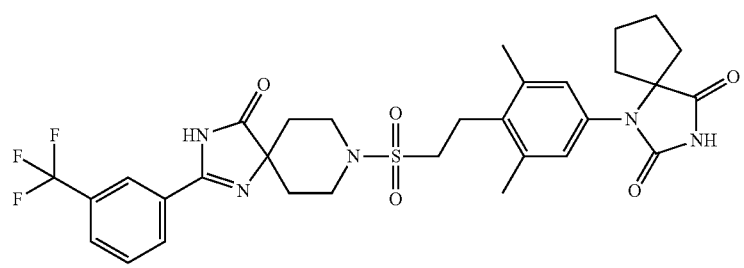

Compound 12

With the use of appropriate starting materials and solvents, 1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-1,3-diazaspiro[4.4]nonane-2,4-dione was obtained by operations similar to those of Example 2.

MS (ESI) m/z=646 (M+H)+. $^1$H-NMR (400 MHz, DMSO-$d_6$) δ: 1.40-1.48 (2H, m), 1.62-1.71 (4H, m), 1.88-1.97 (2H, m), 1.97-2.08 (4H, m), 2.41 (6H, s), 3.03-3.10 (2H, m), 2.29-3.34 (2H, m), 3.38-3.47 (2H, m), 3.72-3.79 (2H, m), 7.06 (2H, s), 7.84 (1H, dd, J=7.6, 7.6 Hz), 8.02 (1H, d, J=7.6 Hz), 8.33 (1H, d, J=7.6 Hz), 8.38 (1H, s)

Test Examples

For the compounds of the present invention, test results on the activity of cAMP production via the human PTH1R, activity of cAMP production via the rat PTH1R, metabolic stability using human liver microsomes, metabolic stability using rat hepatocyte, and calcemic action in TPTX rat models are shown in Test Examples 1 to 5, respectively. Compounds described in WO2010/126030A1, which are shown in Table 2, were used as comparative compounds.

TABLE 2

| Comparative Example | Structural formula |
| --- | --- |
| Comparative Example 1<br>WO2010/126030A1<br>Compound 792 | |
| Comparative Example 3<br>WO2010/126030A1<br>Compound 799 | |
| Comparative Example 3<br>WO2010/126030A1<br>Compound 800 | |
| Comparative Example 4<br>WO2010/126030A1<br>Compound 878 | |
| Comparative Example 5<br>WO2010/126030A1<br>Compound 879 | |

TABLE 2-continued

| Comparative Example | Structural formula |
| --- | --- |
| Comparative Example 6 WO2010/126030A1 Compound 887 | (structure) |

Test Example 1

Measurement of In Vitro cAMP Signal Activity of Compounds Via the Human PTH1R (Peptides)

Human PTH(1-34) and calcitonin were purchased from Peptide Institute, Inc. (Osaka, Japan), dissolved in 10 mM acetic acid to 1 mM and stored in a −80° C. freezer.

(Cell Culture)

Cells were cultured in Dulbecco's modified Eagle's medium (DMEM) supplemented with 10% fetal bovine serum (Hyclone), 100 units/ml penicillin G and 100 μg/ml streptomycin sulfate (Invitrogen Corp) at 37° C. in a humidified atmosphere containing 5% $CO_2$.

cAMP signal transduction analysis utilized LLC-PK1 cells not expressing the PTH1R, and HKRK-B7 cells, that is, LLC-PK1 cells overexpressing the human PTH1R at 9.5× $10^5$ receptors/cell (Takasu et al., J. Bone. Miner. Res. 14:11-20, 1999).

(cAMP Stimulation)

HKRK-B7 or LLC-PK1 cells were seeded into a 96-well plate at 1×$10^5$ cells/well and incubated overnight. On the following day, 50 μl of cAMP assay buffer (DMEM, 2 mM IBMX, 0.2 mg/ml bovine serum albumin, 35 mM Hepes-NaOH, pH 7.4) containing human PTH(1-34) or each compound was added and the plate was placed in a 37° C. incubator. The cells were incubated for 20 minutes. After removing the medium, the cells were washed with 100 μl of cAMP assay buffer once. The plate was placed on dry ice powder to freeze the cells and then removed from the dry ice. The cells were lysed with 40 μl of 50 mM HCl and frozen again on dry ice. The amount of intracellular cAMP produced was measured using a commercially available cAMP EIA kit (Biotrack cAMP EIA system, GE health care).

(Calculation of 20% Effective Concentration (EC20) and 50% Effective Concentration (EC50) in the Measurement of In Vitro cAMP-Inducing Ability)

Analyses were performed using a variable gradient S-shaped dose-response curve equation. The cAMP signaling activity of human PTH(1-34) at 100 nM was defined as 100%, and the concentration at which each compound shows 20% or 50% cAMP signaling activity was calculated as EC20 or EC50.

The results obtained with HKRK-B7 cells are shown in Table 3.

The degree of cAMP response in LLC-PK1 cells was lower than the degree in HKRK-B7 cells.

TABLE 3

| Compound | EC20 (μM) | EC50 (μM) |
| --- | --- | --- |
| Compound 1 | 1.3 | 5.8 |
| Compound 2 | 2.4 | 14 |
| Compound 3 | 1.5 | 7.2 |
| Compound 4 | 1.6 | 7.4 |
| Compound 5 | 1.7 | 8.1 |
| Compound 6 | 2.0 | 9.0 |
| Compound 7 | 1.1 | 4.1 |
| Compound 8 | 1.0 | 3.6 |
| Compound 9 | 2.6 | 12 |
| Compound 10 | 5.0 | 21 |
| Compound 11 | 1.5 | 11 |
| Comparative Example 1 | 1.5 | 4.8 |
| Comparative Example 2 | 3.1 | 13 |
| Comparative Example 3 | 2.0 | 9.0 |
| Comparative Example 4 | >505 | >1000 |
| Comparative Example 5 | 3.1 | 25 |
| Comparative Example 6 | 3.6 | 32 |

Test Example 2

Measurement of the Compounds' In Vitro cAMP Signaling Activity Via the Rat PTH1R Instead of HKRK-B7 cells, LLC-PK46_RATO_PTH1R cells overexpressing rat PTH1R, which were established at Chugai Pharmaceutical, were used to take measurements in a similar manner to Test Example 1.

The results obtained by using LLC-PK46_RATO_PTH1R cells are shown in Table 4.

The EC20 values of in vitro cAMP signaling activity of the rat PTH1 receptor had a good correlation with those of human PTH1R. A good correlation between rat and human was also seen for the EC50 values.

TABLE 4

| Compound | EC20 (μM) | EC50 (μM) |
| --- | --- | --- |
| Compound 7 | 0.5 | 2.4 |
| Compound 8 | 0.4 | 1.9 |
| Compound 10 | 3.0 | 12 |
| Compound 11 | 0.8 | 3.2 |
| Comparative Example 1 | 0.8 | 2.3 |

Test Example 3

Examination of Metabolic Stability Using Human Liver Microsomes

In 0.1 M phosphate buffer (pH7.4), human liver microsomes were incubated with a compound or a comparative example in the coexistence of NADPH at 37° C. for a specified amount of time. The concentration of the parent compound at each reaction time was measured using LC/MS/MS, and inherent clearance (μL/min/mg protein) was calculated from the slope of the reaction time versus residual rate.

<Assay Conditions>
Compound concentration: 1 μM
Microsome: 0.5 mg/mL
NADPH: 1 mM
Reaction time: 0, 5, 15, and 30 minutes The results are shown in Table 5. Compounds 1 to 11 showed high metabolic stability against human liver microsomes in comparison to Comparative Examples 1 to 6.

TABLE 5

| Compound | Clearance (μl/min/mg) |
|---|---|
| Compound 1 | 21 |
| Compound 2 | 38 |
| Compound 3 | 29 |
| Compound 4 | 27 |
| Compound 5 | 37 |
| Compound 6 | 29 |
| Compound 7 | 30 |
| Compound 8 | 35 |
| Compound 9 | 28 |
| Compound 10 | 29 |
| Compound 11 | 19 |
| Compound 12 | 63 |
| Comparative Example 1 | 84 |
| Comparative Example 2 | 61 |
| Comparative Example 3 | 74 |
| Comparative Example 4 | 74 |
| Comparative Example 5 | 112 |
| Comparative Example 6 | 154 |

Test Example 4

Examination of Metabolic Stability Using Rat Hepatocyte

Liver cells were prepared from the liver of rats (SD, female) by a collagenase perfusion method. A compound of the Examples or a Comparative Example was added, and this was incubated at 37° C. for a specified amount of time, followed by addition of a reaction-stopping solution. The concentration of the parent compound at each reaction time was measured using LC/MS/MS, and inherent clearance (μL/$10^6$ cells/min) was calculated from the slope of the reaction time versus residual rate.

<Assay Conditions>
Cell concentration: 1×$10^6$ cells/mL
Compound concentration: 1 μM
Medium: Williams' medium E
Reaction time: 0, 15, 30, 60, 120, and 240 minutes
Reaction-stopping solution: acetonitrile/2-propanol (4/6, v/v)

The results are shown in Table 6. The rat hepatocyte metabolic stability of Compounds 2, 4, 5, 7, 8, 9, 10, and 11 increased compared to Comparative Examples 1, 2, 3, 5, and 6.

TABLE 6

| Compound | Clearance (μl/$10^6$ cells/min) |
|---|---|
| Compound 1 | 7.6 |
| Compound 2 | 3.0 |
| Compound 3 | 17 |
| Compound 4 | 2.2 |
| Compound 5 | 1.0 |
| Compound 6 | 1.4 |
| Compound 7 | 0.9 |
| Compound 8 | 3.0 |
| Compound 9 | 1.8 |
| Compound 10 | 0.3 |
| Compound 11 | −0.6 |
| Comparative Example 1 | 5.8 |
| Comparative Example 2 | 5.9 |
| Comparative Example 3 | 22 |
| Comparative Example 5 | 22 |
| Comparative Example 6 | 22 |

Test Example 5

Calcemic Action in the TPTX Rat Model

Four-week old female Crl:CD(SD) rats were obtained from Charles River Japan (Atsugi Breeding Center), and were acclimated to standard laboratory conditions of 20-26° C. and 35-75% humidity for one week. The rats were given tap water and were fed ad libitum with standard rodent chow (CE-2) (CLEA Japan, Inc.) containing 1.1% calcium, 1.0% phosphoric acid, and 250 IU/100 g of vitamin D3.

TPTX was performed on five-week old rats. Some of the individuals were subjected to sham operation (Sham). Individuals whose serum Ca concentration was less than 8 mg/dL on four days after the operation were selected for use as TPTX rats. On five days after the operation, the rats were assigned to eight TPTX groups and one Sham group (n=5, each group) based on their body weight and serum Ca concentration measured on four days after the operation. The solvent alone was orally administered to the Sham group and the TPTX-Vehicle group at a volume of 10 mL/kg. Each test article was orally administered individually to each TPTX test article group by dissolving it in a solvent at a dose of 30 mg/10 mL/kg. The solvent composition was 10% dimethylsulfoxide (Wako Pure Chemical Industries, Ltd.), 10% Cremophor EL (Sigma-Aldrich Japan LLC), 20% hydroxypropyl-β-cyclodextrin (Nihon Shokuhin Kako Co., Ltd.), glycine (Wako Pure Chemical Industries, Ltd.); and the pH was adjusted to 10. Immediately before administration of each sample, Pre-blood collection was performed, and blood collection was carried out at 2, 6, 10, and 24 hours after administration to measure the serum Ca concentration. Each blood collection was carried out from the jugular vein under isoflurane inhalation anesthesia.

Serum Ca measurement: Serum obtained by centrifugation from the collected blood was measured by using an automatic analyzer TBA-120FR (Toshiba Medical Systems Corporation).

For statistical analysis of the animal studies, data are shown as mean±standard error (SE). Statistical analysis were performed by unpaired test of the SAS Preclinical Package (Ver. 5.00.010720, SAS Institute Japan, Tokyo, Japan). A p-value of <0.05 was regarded as statistically significant. Statistically significant of each test article group comparing to the TPTX-Vehicle group, the Comparative Example 1 group, and the Comparative Example 2 group was shown as #, *, and ƒ respectively.

The Pre-value for the serum Ca concentration was 9.9 mg/dL for the Sham group, and 5.3-6.2 mg/dL for each of the TPTX groups. The serum Ca concentrations for each compound up to 24 hours after administration are shown in FIG. 1 as the average amount of change from the Pre-value. Furthermore, for all of the compounds, the serum Ca concentration peaked at six hours after administration or ten hours after administration of each compound.

Compounds 6, 7, and 8 which have high rat hepatocyte metabolic stability showed large positive changes from the Pre-value, and their oral administration showed strong effects on calcemic action. On the other hand, Compound 1, and Comparative Examples 1 and 2 which have low rat hepatocyte metabolic stability showed smaller positive changes from the Pre-value compared to Compounds 6, 7, and 8. In particular, Compounds 7 and 8 were statistically significant compared to Comparative Examples 1 and 2.

Furthermore, Compounds 6, 7, and 8 which have high rat hepatocyte metabolic stability showed individual maximum values of 7.8 to 8.5 mg/dL at six or ten hours after administration, and achieved the therapeutic target range of serum Ca concentration of 7.6 to 8.8 mg/dL in hypoparathyroidism patients. On the other hand, this therapeutic target range could not be achieved at any of the measurement times for Compound 1, and Comparative Examples 1 and 2 which have low rat hepatocyte metabolic stability.

From the above-mentioned test results, Compounds 6, 7, and 8, which have strong cAMP-signaling activities in cells forced to express rat PTH1R and high stability against metabolic breakdown in rat hepatocytes were found to show strong effects on calcemic action in rats when administered orally. These compounds also have cAMP-signaling activity in cells forced to express human PTH1R and high metabolic stability against human liver microsomes compared to the Comparative Compounds; and they are expected to have high therapeutic effects when administered orally to hypoparathyroidism patients. Furthermore, compounds represented by Formula (1), which have cAMP-signaling activity in cells forced to express human PTH1R and show metabolic stability against human liver microsomes to the same degree as Compounds 6, 7, and 8, are also expected to have high therapeutic effects in hypoparathyroidism patients.

INDUSTRIAL APPLICABILITY

The present invention provides compounds having a strong PTH-like effect and high metabolic stability. The present invention also provides a medicine for the prevention and/or treatment of osteoporosis, fracture, adynamic bone disease, achondronplasia, hypochondroplasia, osteomalacia, osteoarthritis, arthritis, thrombocytopenia, hypoparathyroidism, hyperphosphatemia, tumoral calcinosis or the like, or stem cell mobilization.

The invention claimed is:

1. A compound or pharmacologically acceptable salt or a hydrate or a solvate thereof, wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione.

2. A pharmaceutical composition, which comprises the compound or pharmacologically acceptable salt thereof of claim 1 or a hydrate or solvate or the compound or pharmacologically acceptable salt thereof, as an active ingredient.

3. The pharmaceutical composition of claim 2, which is for use in oral administration.

4. The compound or pharmacologically acceptable salt thereof of claim 1, which is in a hydrate or solvate form.

* * * * *